(12) United States Patent
Müller-Späth et al.

(10) Patent No.: US 9,073,970 B2
(45) Date of Patent: Jul. 7, 2015

(54) CHROMATOGRAPHIC PROCESS FOR ENRICHMENT AND ISOLATION

(71) Applicant: CHROMACON AG, Zurich (CH)

(72) Inventors: Thomas Müller-Späth, Zurich (CH); Guido Ströhlein, Zurich (CH); Lars Aumann, Zurich (CH); Michael Bavand, Lenzburg (CH); Nicole Ulmer, Schlieren (CH)

(73) Assignee: ChromaCon AG, Zurich ( * ) Notice: Subject to any disclaimer, the term of this patent is extended or adjusted under 35 U.S.C. 154(b) by 0 days.

(21) Appl. No.: 14/167,588

(22) Filed: Jan. 29, 2014

(65) Prior Publication Data
US 2014/0248643 A1    Sep. 4, 2014

(30) Foreign Application Priority Data

Mar. 1, 2013 (EP) ..................................... 13157388

(51) Int. Cl.
*G01N 30/44* (2006.01)
*G01N 30/46* (2006.01)
(Continued)

(52) U.S. Cl.
CPC .............. *C07K 1/165* (2013.01); *G01N 30/468* (2013.01); *G01N 30/461* (2013.01); *G01N 30/466* (2013.01); *B01D 15/1864* (2013.01); *B01D 15/40* (2013.01); *C11B 3/008* (2013.01)

(58) Field of Classification Search
CPC . G01N 30/461; G01N 30/466; G01N 30/468; G01N 2030/38; G01N 2030/44
USPC ............. 422/70, 89; 436/161; 702/24, 25, 31; 700/271, 273; 210/656, 198.2; 73/23.35, 23.36, 23.42, 61.52, 61.56, 73/61.57; 95/82, 86; 96/101, 103, 104
See application file for complete search history.

(56) References Cited

U.S. PATENT DOCUMENTS 3,220,164 A * 11/1965 Golay ............................. 95/84
5,630,943 A    5/1997 Grill

FOREIGN PATENT DOCUMENTS

| WO | 2006/116886 A1 | 11/2006 |
| WO | 2010/079060 A1 | 7/2010 |
| WO | 2013/083482 A1 | 6/2013 |

OTHER PUBLICATIONS

Markus Juza et al., Simulated moving-bed chromatography and its application to chirotechnology, TIBTECH, Mar. 2000, pp. 108-118, vol. 18.
(Continued)

*Primary Examiner* — Jan Ludlow
(74) *Attorney, Agent, or Firm* — Sughrue Mion, PLLC

(57) ABSTRACT

A chromatographic process for the enrichment of at least one compound of interest from a mixture is proposed, using chromatographic columns, wherein said process involves a sequence of the following steps: (i) a cyclic accumulation phase, in which the chromatographic columns are alternatingly operated in an interconnected phase, followed by a disconnected phase, wherein subsequently columns exchange places and wherein the phases are carried out sequentially; (ii) a cyclic separation phase, in which the chromatographic columns are alternatingly operated in an interconnected phase, followed by a disconnected phase, wherein after these phases columns exchange places to undergo the next interconnected and disconnected phases; and (iii) an elution phase, in which from the column, which at the end of phase (i) or at the end of phase (ii) contains the compound of interest, is extracted via the outlet.

27 Claims, 11 Drawing Sheets

(51) Int. Cl.
*C07K 1/16* (2006.01)
*B01D 15/18* (2006.01)
*C11B 3/00* (2006.01)
*B01D 15/40* (2006.01)

(56) References Cited

OTHER PUBLICATIONS

European Search Report for EP 13 157 388.3, dated Jun. 25, 2013.

* cited by examiner

CHROMATOGRAPHIC PROCESS FOR ENRICHMENT AND ISOLATION

CROSS-REFERENCE TO RELATED APPLICATION

This application relates to and claims the benefit of priority from European Patent Application number 13 157 388.3, filed on Mar. 1, 2013 the entire disclosure of which is incorporated herein by reference.

TECHNICAL FIELD

The present invention relates to an iterative, cyclic chromatographic process for the enrichment and/or isolation of compounds of interest from mixtures derived from natural extracts and/or chemical and/or biological synthesis.

PRIOR ART

In the following description of prior art as well as of the invention, the terms "enrichment" and "isolation" are of key importance and are therefore defined at first.

The term "Enrichment" in the context of the present description designates a chromatographic process, in which, starting from a mixture comprising a compound of interest as well as further compounds (which are not of interest), the absolute concentration of the compound of interest is increased, either continuously or step-wise. At the end of the chromatographic enrichment process, in the resultant mixture the concentration of the compound of interest is therefore, in absolute terms, higher than it was before. The absolute concentrations of the further compounds that are not of interest are preferably decreased in such a chromatographic process but may also remain constant or may even be increased as well, but preferably not to the same extent as is the concentration of the compound of interest. The degree of desired or required "enrichment" is dependent on the purpose that the compound of interest is needed for. For instance, if a relatively insensitive detection method is used for detecting compounds of interest that are present in the original mixture in concentrations at or below the limit of detection, the degree of required enrichment may be very high.

The term "Isolation" in the context of the present description designates a chromatographic process, in which, starting from a mixture comprising a compound of interest and further compounds (which are not of interest), the concentration of the compound of interest is increased relative to the concentration of the further compounds (which are not of interest) of the mixture. Thus the aim of the "isolation" process is the partial or complete removal of the further compounds from the mixture, while the absolute concentration of the compound of interest in the resultant mixture preferably is higher but may be equal or lower than in the original mixture. Thus "isolation" stands for obtaining the compound of interest with higher purity. The required purity level depends on the purpose of the "isolation". For instance, if the compound of interest is isolated for an assay that is very sensitive to other interfering compounds, the required "isolation" may be very high.

Ideally, in a chromatography process, both enrichment and isolation are obtained simultaneously, meaning that the compounds of interest are obtained with an absolute concentration and a purity that is higher than the one of the feed mixture.

However, mostly in standard chromatographic processes the simultaneous enrichment and isolation of compounds from a multi-compound mixture is not achieved in a satisfactory manner. This is due to the fact that generally in traditional single column chromatographic processes (excluding affinity chromatography) the compound of interest is present in low concentration and flanked by a number of interfering impurities (further components not of interest) with similar adsorptive and/or molecular properties. Attempts to obtain enrichment by increasing the amount of supplied feed mixture per volume of stationary phase (increased load) generally lead to a stronger overlap of the compounds of interest and the interfering impurities; therefore these approaches are worsening the purity. Generally, an improvement in enrichment compromises the isolation, i.e. the resultant degree of purity. The increased overlapping at increased load is due to the adsorptive properties of the compounds of the feed mixture on the chromatographic stationary phase (isotherm effects) and to transport properties (mass transfer properties) leading to peak deformation and peak broadening, respectively. These effects hamper the enrichment and isolation of compounds of interest by both analytical and preparative chromatography. As a consequence, in analytical chromatography (where small amounts are loaded), enrichment of the compound of interest generally cannot be obtained by simply increasing the load. In order to obtain larger amounts of compounds of interest without compromising the resolution of the separation, either the chromatography column may be scaled up keeping the same low load as in analytical chromatography (which is generally economically not feasible due to the high costs of the analytical chromatographic stationary phase and the low productivity of analytical chromatography) or the analytical procedure may be run repeatedly. As stateof-the-art, in most cases the latter is carried out ("numberup"), which implies a large effort in terms of sampling and handling and, at the current state, cannot be fully automated with economically reasonable effort. Furthermore the repeating of analytical chromatography only delivers the compounds of interest with low concentrations as analytical chromatography is generally strongly diluting and consequently requires time- and resource-consuming subsequent steps to increase the absolute concentration of the compound of interest. Moreover, when loading small amounts of sample as in analytical chromatography, sufficient enrichment may not be obtained and the concentration of potential compounds of interest may remain below the detection limit of the analytical instruments used. Thus, by "number-up" isolation and enrichment are decoupled. A further problem is that it can be very difficult and burdensome or even practically almost impossible to increase the low concentration of a highly purified compound of interest subsequent to the chromatographic process to a concentration value suitable for the further uses/ analytical purposes. In the case of isolation of compounds of interest that completely overlap in a chromatogram with other compounds of the mixture (a case which is frequently observed in practice), only limited purity can be obtained by traditional single column analytical chromatography. In some cases the enrichment and the purity of the compound of interest can be increased if the purest sample of a first chromatography run is mixed with feed mixture or other pure samples before re-loading it onto the chromatography column (re-chromatography), which is not attractive as it implies the risk of losing partially purified compounds of interest in case of failure of the chromatography run, apart from being tedious and time-consuming. Preparative single column chromatography suffers from the same disadvantage but is better suited for enrichment since preparative chromatography stationary phases generally feature a larger capacity and larger particles, allowing for higher throughput. However, due to the larger particles and broader particle size distributions, the mass transfer properties are worse than for small-particle analytical stationary phases, strongly reducing the achievable purity.

Examples for multi-compound mixtures that pose the aforementioned challenge of obtaining simultaneous enrichment and isolation are frequently found in the application field of drug product characterization and impurity profiling in drug development and include the enrichment and isolation of product related impurities. Specific examples include but are not limited to the isolation and enrichment of peptide compounds produced by chemical synthesis, DNA/RNA fragments, therapeutic protein isoforms, fragments, aggregates and glyco-forms.

Additional examples are found in the application field of discovery of drug leads in compound mixtures derived from bio/chemical or from natural extracts. Many of these mixtures contain a multitude of potentially active substances which are present in very low concentration, making detection impossible or at least very difficult, not to speak of isolation in sufficient amounts for further characterization.

Further examples are found in the field of diagnostics such as the isolation of biomarkers from biological fluids and analysis of the plasma proteome.

Multicolumn chromatography processes allow for the purification of compounds of interest with high yield and purity. However, in most cases, the compounds of interest are accompanied by impurities with weaker and stronger adsorptive properties, which are overlapping with the compounds of interest in a representative chromatogram, requiring a ternary separation (the compounds of interest are in the center fraction). Since state of-the-art simulated moving bed chromatography (SMB) processes are suitable only for binary and pseudo-ternary separations, they cannot achieve satisfactory simultaneous isolation and enrichment of the compounds of interest.

Moreover, the task of simultaneous isolation and enrichment can, at least for certain fields of application, also not be achieved in an optimal manner by multicolumn countercurrent solvent gradient purification (MCSGP, see in particular WO 2006/116886) although MCSGP is suitable for ternary and higher order separations. In MCSGP, the feed mixture to be separated is cyclically introduced into the separation process and the compounds of interest are cyclically removed from the process thus a constant product profile is maintained which however allows only for isolation of a few compounds with low enrichment.

SUMMARY OF THE INVENTION

The two processes SMB and MCSGP have been designed for the cyclic purification/production of compounds of interest with a constant product quality profile, which is of high interest in industrial larger-scale purification processes. These processes therefore are often not the optimal processes for the abovementioned application fields, i.e. for simultaneous enrichment and isolation. By internal recycling and re-processing of impure side-fractions SMB/MCSGP compensate for the effects of peak-broadening caused by isotherm and mass transfer effects. However, by constantly feeding and isolating the compounds of interest, these processes do not allow for significant enrichment (for SMB see e.g. Juza M, Mazzotti M, Morbidelli M, Simulated moving bed chromatography and its application to chirotechnology. 2000. Trends in Biotechnology 18, p 108-118; for MCSGP see WO 2006/116886). Furthermore these processes are either not designed for isolation of multiple compounds of interest (SMB) or require significant hardware effort for multiproduct isolation (MCSGP, see also WO 2010/079060).

The herein presented invention proposes a new method for the enrichment of compounds of interest using simulated moving bed technologies, and in particular it relates to an iterative, cyclic twin column chromatographic process suitable for simultaneous enrichment and isolation of compounds from a mixture. The expression twin column however including situations where one or both of the members of the twin can also be a series or a parallel arrangement of two or more columns.

Generally speaking therefore, the invention relates to a chromatographic process for the enrichment of at least one compound of interest (X) from a mixture (F) comprising said at least one compound of interest (X) as well as at least one further compound (W, C, S), which is not of interest, using at least two chromatographic columns, wherein said iterative process at least involves a sequence of the following steps:

(i) a cyclic accumulation phase, in which the at least two chromatographic columns are alternatingly operated in an interconnected phase (IC), followed by a disconnected phase (B), wherein after these two phases the first and second column or group of columns exchange positions to undergo the next interconnected (IC) and disconnected phases (B) (in case of intermittent feeding exchange of positions can also only take place after two couples of interconnected (IC) and disconnected phases (B));
wherein said two phases of the cyclic accumulation phase are carried out sequentially M times with M>1;

(ii) a cyclic separation phase, in which the at least two chromatographic columns are alternatingly operated in an interconnected phase (IC), followed by a disconnected phase (B), wherein after these two phases the first and second column or group of columns exchange positions to undergo the next interconnected (IC) and disconnected phases (B) (in case of intermittent extraction exchange of positions can also only take place after two couples of interconnected (IC) and disconnected phases (B)); wherein said two phases are carried out sequentially N times with N≥0;

(iii) an elution phase, in which from the column or group of columns, which at the end of phase (i) or, in case of N>0 at the end of phase (ii) contains the at least one compound of interest (X), said at least one compound of interest (X) is extracted via the outlet.

Exchange of positions of the columns in the context of the cyclic accumulation phase and of the cyclic separation phase means that the two columns (or groups of columns), after an IC an a B phase, are exchanged such that the former upstream column (or group of columns) becomes the downstream column (or group of columns), and the former downstream column (or group of columns) becomes the upstream column (or group of columns). The exchange can be effected by respective valve switching.

In contrast to the prior art processes such as e.g. MCSGP (WO 2006/116886), the compound of interest (X) is thus not taken out of the system in all steps, but the process involves steps in which selectively compound of interest (X) is left in the system under continued feeding while the further compounds can preferably be discharged from the system. The result is that the absolute concentration of the compound of interest (X) in the final eluate is higher than in the feed mixture and at the same time, if the further compounds are concomitantly discharged from the system, the relative concentration of the compound of interest (X) with respect to the further compounds which are not of interest is dramatically increased. So the result is an enrichment, which can even be carried to an isolation, where the compounds which are not of interest are essentially fully removed from the system, in particular if N is chosen to be larger than 0, preferably larger than 1 or 2.

It should be noted that said disconnected phase (B, batch mode) and said interconnected phase (IC) can be either sequentially as illustrated below and as realized if using two columns, but it is also possible to carry out the phases synchronously, in which case more than two columns are required.

In the cyclic phases of the process (i.e. the accumulation phase and/or the separation phase), the columns are operated in interconnected configurations "IC" and in disconnected configurations "B". In the interconnected configuration the outlet of the upstream column is fluidly connected with the inlet of the downstream column allowing for compounds to be washed from the upstream column into the downstream column (or group of columns, respectively). In the disconnected configuration the columns have independent fluid inlets and outlets (Batch mode of the columns).

During the cyclic phases of the process, disconnected and interconnected column configurations alternate after defined time periods. These two configurations are referred to as "disconnected phases" (B) and "interconnected phases" (IC) in the following. Once a sequence of interconnected (IC) and disconnected (B) phases has been completed, the columns switch positions such that the upstream column becomes the downstream column and vice versa and the sequence is repeated. In practice, the switch is accomplished by changing the fluid path by means of valves rather than physically moving the columns. After the sequence IC→B has been repeated and the columns have switched positions again, the columns are at their initial positions again, i.e. the columns having been upstream initially are back in the upstream position and the columns having been downstream initially are back in the downstream column position. The sequence of one interconnected (IC) and one disconnected (B) states is called a "switch" while two sequential switches form a "cycle".

After or within a switch time t* the columns are moved in their positions in a counter direction to the general direction of flow of the solvent. The switch time is thus the time it takes for one sequence of one interconnected (IC) and one disconnected (B) state.

Somewhat more specifically phrased, said iterative process preferably at least involves a sequence of the following steps:
(i) said cyclic accumulation phase, in which the at least two chromatographic columns are alternatingly operated in
 a. an interconnected phase (IC), in which an outlet of a first upstream column or group of columns is fluidly connected to an inlet of a second downstream column or group of columns such as to transfer at least a fraction of the compound of interest (X) from the upstream to the downstream column or group of columns; followed by
 b. a disconnected phase (B), in which the first upstream column or group of columns and the second downstream column or group of columns are not fluidly connected,
  wherein at least one of the columns or group of columns is fed with said mixture (F) via its inlet, and wherein via the outlet of at least one of said first and/or second column or group of columns the at least one further compound (W, C, S), which is not of interest, is discharged from the system;
 wherein after these two phases (IC, B) the first and second column or group of columns exchange positions to undergo the next interconnected (IC) and disconnected phases (B) to form a full accumulation cycle;
 wherein said two phases of the cyclic accumulation phase are carried out sequentially M times with M>1 (wherein it is noted that it is possible in this cyclic accumulation phase and preferred, that via the outlet of at least one of said first and/or second column or group of columns in at least one of said phases (IC, B) the at least one further compound (W, C, S), which is not of interest, is discharged from the system);
(ii) said cyclic separation phase, in which the at least two chromatographic columns are alternatingly operated in
 a. an interconnected phase (IC), in which an outlet of a first upstream column or group of columns is fluidly connected to an inlet of a second downstream column or group of columns such as to transfer at least a fraction of the compound of interest (X) from the upstream to the downstream column or group of columns; followed by
 b. a disconnected phase (B), in which the first upstream column or group of columns and the second downstream column or group of columns are not fluidly connected,
  wherein none of the columns or group of columns is fed with mixture (F) via its inlet, but wherein via the outlet of at least one of said first and/or second column or group of columns the at least one further compound (W, C, S), which is not of interest, is discharged from the system;
 wherein after these two phases (IC, B) the first and second column or group of columns exchange positions to undergo the next interconnected (IC) and disconnected phases (B) to form a full separation cycle;
 wherein said two phases of the cyclic separation phase are carried out sequentially N times with N≥0;
(iii) said elution phase, in which from the column or group of columns, which at the end of phase (i) or, in case of N>0 at the end of phase (ii) contains the at least one compound of interest (X), said at least one compound of interest (X) is extracted via the outlet.

So the invention preferably proposes a chromatographic process for the isolation of compounds of interest X from a mixture comprising X and at least one other species or further compound, often a mixture of other species, which are not of interest, comprising at least two columns and at least two consecutive phases, namely
(i) a cyclic phase for the accumulation of compounds of interest in which at least two chromatographic columns are periodically interconnected (IC) and disconnected (B) in order to transfer the compounds of interest from one column to the other during the interconnected period and in order to apply fresh feed mixture to one column and to remove the compounds that are not of interest from the other column during the disconnected period
(iii) a final elution phase in which the compounds of interest are recovered from the columns.

The cyclic phase for accumulation (i) can optionally be followed by a cyclic separation phase (ii) wherein at least two chromatographic columns are periodically interconnected and disconnected in order to transfer the compounds of interest from one column to the other during the interconnected period and no feed mixture is applied to any of the columns during the disconnected period and wherein the cyclic separation phase is succeeded by a final elution phase (iii) in which the compounds of interest are recovered from the columns.

According to a preferred embodiment, in the disconnected phase (B) of the accumulation phase (i) the column or group of columns, which in the preceding interconnected phase (IC) was the downstream column or group of columns is fed with mixture (F) via its inlet. According to yet another preferred embodiment, in the disconnected phase (B) of the accumulation phase (i) the column or group of columns, which in the preceding interconnected phase (IC) was the upstream column or group of columns is fed with mixture (F) via its inlet, or this column is fed with mixture (F) via its inlet after initially having been cleaned and equilibrated.

In the interconnected phase (IC) of the accumulation phase (i) the properties of the stream exiting the upstream column or group of columns can be changed, preferably by introducing buffer, solvent and/or modifier into the fluid path between the upstream column or group of columns and the downstream column or group of columns.

In the disconnected phase (B) of the accumulation phase (i) preferably the column or group of columns, which is fed with mixture (F) via its inlet, is in a first phase of the disconnected phase (B) fed with mixture (F) via its inlet, and in a second phase of the disconnected phase (B) is fed with buffer, and/or solvent and/or modifier without mixture (F).

In the elution phase (iii) the eluted compound of interest (X) can be subjected to outlet fractionation.

In the elution phase (iii) the compound of interest (X) can be eluted in a configuration, in which an outlet of a first upstream column or group of columns is fluidly connected to an inlet of a second downstream column or group of columns, preferably by using the arrangement of the columns of the preceding interconnected phase (IC), or of the interconnected phase (IC), which would follow the preceding disconnected phase (B).

In the case where the compound of interest (X) is a weakly adsorbing fraction (W) of the chromatographic elution profile, in the disconnected phase (B) of the cyclic accumulation phase (i), and in case of N>0 also of the cyclic separation phase (ii), the column or group of columns which is not fed with mixture (F) is preferably operated so as to elute the at least one stronger adsorbing, further compound (C, S), which is not of interest, and preferably is also equilibrated.

In the case where the compound of interest (X) is a strongly adsorbing fraction (S) of the chromatographic elution profile, in the disconnected phase (B) of the cyclic accumulation phase (i), and in case of N>0 also of the cyclic separation phase (ii), the column or group of columns which is not fed with mixture (F) is preferably operated so as to be equilibrated, and the column or group of columns which is fed with mixture (F) is operated such as to elute the at least one further weaker adsorbing compound (W, C), which is not of interest. Additionally or alternatively, W, C may be removed during the subsequent interconnected phase (IC).

In the case where the compound of interest (X) is an intermediately adsorbing fraction (C) in the disconnected phase (B) of the cyclic accumulation phase (i), and in case of N>0 also of the cyclic separation phase (ii), the column or group of columns which is not fed with mixture (F) is operated so as to elute at least one further compound (S), which is not of interest, and preferably is further equilibrated, and the column or group of columns which is fed with mixture (F) is operated such as to elute at least one further compound (W), which is not of interest, or to the at least one further weaker adsorbing compound (W, C) is washed out in the subsequent interconnected phase (IC).

It should be noted that in this latter scenario the process can also be used for enrichment in a situation where the compound of interest is completely covered by a broad profile of undesired compounds. Running the process in this case by repeatedly cutting off the left and right side tails of this broad covering profile under continued feeding leads to a simultaneous enrichment and isolation of the desired compound since the undesired compounds are successively depleted.

In any of these cases the degree, to which next to the least one further compound (W, C, S), which is not of interest, also a part of the compound of interest (X) is eluted, is preferably adapted as a function of the desired enrichment and/or isolation of the compound of interest (X) in the final elute of the elution phase (iii). It is possible to choose the cut-off such that no overlapping of the compound of interest (X) with the undesired compounds is kept in the system, which however leads to a continuous partial drain of the compound of interest (X) from the system. The cut-off can be chosen such that the full overlapping of the compound of interest (X) with the undesired compounds is kept in the system, which however will lead to a lower purity or to more necessary cycles M and/or N. Also a variable cutoff strategy is possible, e.g. by choosing the cut-off such that the full overlapping of the compound of interest (X) with the undesired compounds is kept in the system in the cyclic accumulation phase, while for the separation phase the cut-off is chosen such that no overlapping of the compound of interest (X) with the undesired compounds is kept in the system.

Liquids, gases or supercritical fluids can be used as mobile phases.

A phase, in particular the elution phase (iii), may involve a change of the mobile phase composition over time.

According to a preferred embodiment of the proposed process, M is larger 2, preferably M is larger 6, and most preferably M is larger 10. Preferably the absolute concentration of the compound of interest (X) in the resultant eluate of the elution phase (iii) is higher than the one in the feed mixture (F).

According to yet another preferred embodiment, N>0, preferably N>2, most preferably N>4.

Further the invention relates to a use of the chromatographic process as outlined above, wherein the fractions of the compounds of interest recovered in the final elution phase are subjected to further processing and/or online analysis, which is carried out either manually or automatically. The further processing may include analysis of the fractions, and/or includes a chromatographic method, and/or include mass spectrometry, and/or include the matching against a database, and/or include the use of a binding assay, and/or include the use of a cell based assay.

Furthermore the invention relates to a use of the chromatographic process as outlined above, to enrich, isolate, or discover compounds of interest, wherein preferably the process is carried out systematically on target regions of an entire chromatographic profile obtained from processing the mixture containing the compounds of interest.

Furthermore the invention relates to a use of the chromatographic process as outlined above, wherein the method is carried out iteratively by subjecting different target fractions of the chromatogram containing compounds of interest (X) to the process or by subjecting the same target fraction more than once.

The process thus, generally speaking, comprises a cyclic accumulation phase, an optional cyclic separation phase and a final elution phase, which steps are executed sequentially as schematically indicated in FIG. 1 for the twin-column embodiment of the process.

During the cyclic phases of the process, the columns successively occupy 4 different positions (1-4), which correspond to different process tasks.

During one switch, one column performs the tasks of positions 1,2 while the other column performs the tasks of positions 3,4. A cycle corresponds to a column having occupied four different positions (1-4) in series. The columns switch positions in the order . . . →1→2→3→4→1→2→ . . . . Thus, within a cycle each column has passed through each possible position in the process flow sheet and has returned to its original position.

The cyclic accumulation phase (i) serves for enrichment of the compounds of interest and for simultaneous removal of impurities. This phase includes an alternating sequence of disconnected phases (B) and interconnected phases (IC) as described below with feed supply.

In the disconnected phase B of the cyclic accumulation phase the feed mixture is applied to one of the chromatographic columns or to both columns and the compounds of interest of the mixture adsorb in the column(s) while compounds which are not of interest are washed out. Typically, the feeding step is followed by a separate washing step for removal of impurities. Additionally a modifier gradient may be run for removal of impurities. Simultaneously, from the other column compounds that are not of interest are either washed out (cleaning) and the column is equilibrated (mainly in case where the most weakly adsorbing compounds are the products of interest or a the intermediate compounds are the products of interest) or the column is just equilibrated by means of suitable solvents or buffers (mainly in case where the most strongly adsorbing compounds are the products of interest). Afterwards, fresh feed solution may be loaded onto the cleaned and equilibrated column. Additional washing, gradient, cleaning, waiting and/or equilibration steps may be carried out on both columns while the columns are in disconnected configuration. Thereby it may be, under certain circumstances, important to ensure that the column that becomes the downstream column in the subsequent interconnected phase is at least cleaned and equilibrated before entering the interconnected phase, and optionally loaded. The single tasks of the columns in the batch mode positions can thereby be distributed such that the column utilization is optimized and potential waiting times are minimized. As an example, in the case, that the sub-tasks have the following durations: column 1: feeding: 3 min, washing: 5 min; column 2: cleaning: 2 min, equilibration 6 min; 3 min+5 min=2 min+6 min=8 min. Thus columns 1 and 2 are occupied for the same time duration and the time utilization is optimal.

In contrast, if a more thorough cleaning is required and the cleaning time can be 6 min instead of 2 min, column 2 can be occupied for 6 min+6 min=12 min while column 1 can be occupied for 8 min. Instead of introducing a wait time of 4 min to match the occupancy of the two columns, for instance a gradient of 4 min can be started on column 1 in order to remove impurities. In another case, assuming that the washing step that follows the loading step is time limiting, the feed can take place in the column position where cleaning and equilibration took place. During the optional waiting steps (which should be minimized) no solvent flow is present in one of the columns.

In the interconnected phase IC of the cyclic accumulation phase the compounds of interest are washed from the upstream column into the downstream column where they adsorb. The desorption of the compounds of interest from the upstream column is realized by means of a suitable mobile phase (buffer/solvent). The adsorption in the downstream column is made possible by changing the physico-chemical properties of the stream that exits the upstream column, for instance by inline dilution with another stream.

The cyclic separation phase (ii) serves for removal of impurities and for separation of the compounds of interest. This optional phase includes an alternating sequence of disconnected phases (B) and interconnected phases (IC) without feed supply.

In the cyclic separation phase, the same column configurations and phases as in the cyclic accumulation phase are used. However, the application of feed solution is turned off. Since the impurity removal in the disconnected state remains, the compounds of interest that stay in the system are further purified. In addition, in the interconnected state, the compounds of interest are better assorted and separated among themselves.

In order to optimize impurity removal and separation among the compounds of interest the flow rate, mobile phase compositions and the IC and B phase durations may be selected differently compared to the cyclic accumulation phase.

The purpose of the final elution phase (iii) is the isolation of the compounds of interest. In the final elution phase the columns are present in only one configuration. The compounds of interest are washed out of the respective chromatographic column by means of suitable mobile phase (buffer/solvent). In order to further improve the separation, the column that does not contain the compounds of interest may be cleaned, equilibrated and interconnected with the column that contains the compounds of interest whereby the equilibrated column is placed in the downstream position. Subsequently the compounds of interest are washed out of the upstream column through the downstream column whereby the separation is further improved compared to the direct washing out without using the other column.

Typically the stream leaving the column is fractionated to isolate different compounds of interest in different fractions. In parallel the chromatographic profile is typically monitored using suitable online analytics. The information from online analytics may be also used to adjust the fractionation intervals. The enriched and isolated compounds of interest are now available for further analysis or processing. Optionally, in the elution phase, a device for online measurement may be coupled to the device running the process. In contrast to the other phases of the process the final elution phase is only carried out once. The mobile phase flow rates, compositions and the duration of the final elution phase may be significantly different from the conditions used in the IC and B phases in order to optimize the resolution of the compounds of interest. The compounds of interest fed to the process during the cyclic accumulation phase are recovered in the final elution phase with high purity.

The complete process flow sheet including cyclic accumulation, separation and final elution phase is schematically shown in FIG. 1. The number of switches, M (with M being a positive integer equal or larger than 2), run in the accumulation phase is dependent on the degree of desired enrichment of the compounds of interest and can be estimated from their concentrations in the feed and the feed volume. During the accumulation phase the feed supply is active. The number of switches, N (with N being a non-negative integer), run in the separation phase is dependent on the degree of desired purity of the compounds of interest. In the case where the required purity of compounds of interest is low, the cyclic separation phase may be skipped (N=0).

Instead of terminating the accumulation phase and the separation phase after a complete cycle (corresponding to an even number of switches), respectively, the phases may be terminated also after a half-cycle (switch). In the latter case, the phases following the cyclic accumulation phase and the cyclic separation phase, respectively, need to be adjusted in order to elute the compounds of interest from the correct column.

In the final elution phase, the column containing the compounds of interest is eluted and the enrichment and isolation process is completed.

In the present invention, in contrast to other cyclic chromatographic processes such as MCSGP and SMB the compounds of interest are isolated only during the final elution phase and not in a cyclic manner. This corresponds to an absence of the β section in the processes described in WO-A-2006/116886. This feature allows for a much larger enrichment than can be obtained with MCSGP since no cyclic steady state is reached. MCSGP does not feature a separation and a final elution phase, since product is withdrawn from the process with a constant purity profile once cyclic steady state has been reached. In contrast to SMB, the novel process is capable of isolating compounds also from ternary mixtures with product overlaps and it is capable of running solvent gradients other than step gradients, which is of major importance in the described application fields.

Through the enrichment and the simultaneous repeated removal of interfering compounds, the presented process allows for discovery and isolation of compounds that were previously not detectable using state-of-the-art chromatographic techniques. The process can be integrated perfectly into existing discovery processes by coupling it to highly sensitive analysis processes.

Thus, MCSGP/SMB and the novel process are applicable in rather different environments: MCSGP primarily in the continuous production of compounds with constant product quality throughout the chromatographic process (for instance in pharmaceutical production); and the novel chromatographic process in the enrichment and isolation of compounds in a discovery and research environment (for instance pharmaceutical screening, pharmaceutical development, and pharmaceutical characterization).

In the following application cases are described wherein the compounds of interest are a.) accompanied only by late eluting impurities, b.) accompanied only by early eluting impurities, c.) accompanied by both early and late eluting impurities. For the sake of the examples a profile is assumed with a weakly adsorbing (fast eluting) fraction designated with W, an intermediate fraction C, and a strongly adsorbing (slow eluting) fraction designated with S. The fraction of interest is then designated by replacing these with X, depending on whether the fraction of interest or compound of interest is the weak, intermediate or strong fraction.

For the case where the compounds of interest are flanked by only late eluting impurities (a.), essentially requiring a binary separation, the detailed process schematic of the accumulation phase is described in FIG. 2. The columns (1, 2) carry out the tasks of positions 1,3 (interconnected "IC" state tasks) and 2,4 (disconnected, batch "B" state tasks) simultaneously. The process tasks are executed in the order →2→3→4→1 → . . . (column 1) and 3→4→1→2→3→ . . . (column 2) and the columns switch positions in that order. The vertical dashed lines in FIG. 2 schematically indicate the section borders and define the solvent conditions (e.g. portions of the gradient) to be run in that section. In the interconnected state, the compounds of interest, X, are internally recycled from the upstream to the downstream column (positions 1, 3). The compounds C, which are not of interest, may be partially internally recycled (depending on the overlap with X) but for the largest part remain in the upstream column together with compounds S which are also not of interest. In order to bind X on the downstream column, the properties of the stream exiting the upstream column are changed (e.g. by inline dilution with a stream QC) such that the properties of the mixed stream favor the adsorption of X. After having completed the interconnected state tasks 1, 3 the columns are disconnected and the process tasks 2, 4 are executed, respectively.

Task 2 comprises the supply of feed solution containing X, C, S to the downstream column. Additionally task 2 may comprise washing steps that keep X within the downstream column. In parallel to task 2, task 4 is executed on the upstream column. Task 4 comprises a removal of C and S and a re-equilibration of the column. Depending on the overlap of X and C, also a part of X may be removed.

Once the tasks 2 and 4 have been completed, the columns switch positions such that the upstream column becomes the downstream column and vice versa.

The columns are then interconnected again and the process tasks of IC and B are repeated with the columns in the opposite order. Once IC and B have been completed, the columns switch positions again such that the upstream column becomes the downstream column and vice versa. The columns are now in their original positions, marking the completion of one cycle.

For the case where the compounds of interest are flanked by only early eluting impurities (b.), essentially requiring a binary separation, the detailed process schematic of the accumulation phase is described in FIG. 3. The two columns (1, 2) carry out the tasks of positions 1,3 (interconnected "IC" state tasks) and positions 2,4 (disconnected, batch "B" state tasks) simultaneously. The process tasks are executed in the order 1→2→3→4→1→ . . . (column 1) and 3→4→1→2→3→ . . . (column 2) and the columns switch positions in that order. In the interconnected state, the compounds of interest, X, are internally recycled from the upstream to the downstream column (positions 1, 3). The compounds C, which are not of interest, may be partially internally recycled (depending on the overlap with X) but for the largest part should have been removed already in a washing or gradient step following the loading (task 2). In order to bind X on the downstream column, the properties of the stream exiting the upstream column are changed (e.g. by inline dilution with a stream QC) such that the properties of the mixed stream favor the adsorption of X. After having completed the interconnected state tasks 1, 3 the columns are disconnected and the process tasks 2, 4 are executed, respectively.

Task 2 comprises the supply of feed solution containing W, C, X to the downstream column. The loading of the feed is followed by a washing step, carried out in order to remove W and the C. As indicated in the Figure, also a modifier gradient may be used in task 2 in order to remove W and C. In parallel to task 2, task 4 is executed on the upstream column. Task 4 comprises a more thorough cleaning if required, but at least re-equilibration of the column.

Once the tasks 2 and 4 have been completed, the columns switch positions such that the upstream column becomes the downstream column and vice versa.

The columns are then interconnected again and the process tasks of IC and B are repeated with the columns in the opposite order. Once IC and B have been completed, the columns switch positions again such that the upstream column becomes the downstream column and vice versa. The columns are now in their original positions, marking the completion of one cycle.

In the case where the compounds of interest are flanked by both early and late eluting impurities (c.), essentially requiring a ternary separation, the detailed process schematic of the accumulation phase is described in FIG. 4. The two columns (1, 2) carry out the tasks of section 1,3 (interconnected "IC" state tasks) and 2,4 (disconnected, batch "B" state tasks) simultaneously. The process tasks are executed in the order →2→3→4→1→ ... (column 1) and 3→4→1→2→3→ ... (column 2) and the columns switch positions in that order. In the interconnected state, the compounds of interest, X, are internally recycled from the upstream to the downstream column (positions 1,3). The compounds W, which are not of interest, may be partially internally recycled (depending on the overlap with X) but for the largest part should have been removed already in a washing or gradient step following the loading (task 2). In addition, the compounds S, which are not of interest, may be partially internally recycled (depending on the overlap with X) but for the largest part remain in the upstream column.

In order to bind X on the downstream column, the properties of the stream exiting the upstream column are changed (e.g. by inline dilution with a stream QC) such that the properties of the mixed stream favor the adsorption of X. After having completed the interconnected state tasks 1, 3 the columns are disconnected and the process tasks 2, 4 are executed, respectively. Task 2 comprises the supply of feed solution containing W, X, S to the downstream column. Additionally task 2 may comprise washing steps. As indicated in the Figure, also a modifier gradient can be used in task 2 in order to remove W. Depending on the overlap of W and X, also a part of X can be removed. In parallel to task 2, task 4 is executed on the upstream column. Task 4 comprises a removal of S and a re-equilibration of the column. Depending on the overlap of X and S, also a part of X may be removed.

Once the tasks 2 and 4 have been completed, the columns switch positions such that the upstream column becomes the downstream column and vice versa.

The columns are then interconnected again and the process tasks of IC and B are repeated with the columns in the opposite order. Once IC and B have been completed, the columns switch positions again such that the upstream column becomes the downstream column and vice versa. The columns are now in their original positions, marking the completion of one cycle.

The compounds of interest may also include multiple compounds. As an example the accumulation phase of the process is schematically illustrated in FIG. 5 for a mixture of four compounds of interest X1, X2, X3, and X4. In the interconnected state IC, X1 and X4 are partially recycled and X2 and X3 are completely recycled from the upstream to the downstream column. In the subsequent disconnected state B, the remaining portions of X1 and X4, which are overlapping with early eluting impurities W and late eluting impurities S are removed from the columns along with W and S, respectively. The complete or partial removal of the overlapping part ensures that compounds which are not of interest are not enriched. The process tasks for X containing multiple compounds are performed as described above (c.) and the description is also valid for the cases illustrated in FIG. 2 and FIG. 3.

It is worth noting that the column switch (upstream column and downstream columns switch positions) may also be performed after the columns have completed the interconnected state tasks (1,3). The concept of upstream and downstream positions does not apply when the columns are in the batch mode position. Thus, the representation in FIGS. 1-5 and 12 showing column 1 in the downstream position in the batch state is arbitrary. However, it is important that the column that has been in the upstream position in the interconnected state fulfils at least the task of cleaning (task 4) in the subsequent batch state and that the column that has been in the downstream position in the interconnected state fulfils at least the task of feeding or washing (task 2) in that batch state. After that it is important that the column that has fulfilled at least the task of cleaning in the batch state becomes the downstream column in the subsequent interconnected state (task 1) and that the column that has fulfilled the task of feeding or washing becomes the upstream column in that interconnected state (task 3).

The compounds of interest X1, X2 may also be early and late eluting, embracing a center eluting compound C which is not of interest. This includes the case where only one compound of interest is present that completely X overlaps with the impurities C but extends beyond the peak of C so that it has a relatively high purity in the front and in the tail of the profile as indicated schematically in FIG. 12. In this case, the cyclic accumulation and separation phases comprise two interconnected states for the internal recycling of the early and the late eluting compounds of interest, respectively, and two disconnected states with one disconnected state for feeding one column and removal of component C from the other column and the other batch state for washing one column and cleaning/equilibrating the other column.

This intermittent feeding can be realized, generally speaking, in that in the cyclic accumulation phase (i) in only every second disconnected phase (B) a column is fed with mixture (F) via its inlet, and wherein only after four phases (IC, B) the first and second column or group of columns exchange positions to undergo the next interconnected (IC) and disconnected phases (B) of the cyclic accumulation phase.

This intermittent extraction can be realized, generally speaking, in that in the cyclic separation phase (ii) in only every second disconnected phase (B) at least one further compound (C), which is not of interest, is discharged from the system, and wherein only after four phases (IC, B) the first and second column or group of columns exchange positions to undergo the next interconnected (IC) and disconnected phases (B) of the cyclic accumulation phase The operating parameters (elution volumes, modifier concentrations) for the novel process can be derived from a chromatogram from a single column chromatographic run. Once the section borders have been allocated, the elution volumes to be transported through the columns at the different positions are defined. Thus, if the same flow rate as in the single column chromatographic run was chosen, the time period would be determined. Moreover, the modifier concentrations to be applied in the novel process are equivalent to the modifier concentrations at the section borders of the single column process.

As to further preferred embodiments, these are the following:

The presented process comprises two chromatographic columns or multiple columns interconnected divided into two serially connected column groups. In the following, the term "column" refers either to a single column or multiple columns connected in series. The process comprises at least one, preferably two cyclic phases and one final phase. The phases are carried out sequentially with the cyclic phases, if present, comprising at least one switch (half a cycle). In the cyclic phases the chromatographic columns (or column groups) are grouped into at least two individual configurations and in the final phase the columns are grouped into at least one individual configuration.

In a preferred embodiment, in the interconnected configurations a stream of mobile phase washes out the compounds of interest from the upstream column with the proviso that the properties of the stream exiting the upstream column are changed before entering the downstream column, providing cumulative mobile phase conditions under which the compounds of interest re-adsorb in the downstream column. In a preferred embodiment the re-adsorption of the compounds of interest in the downstream column is achieved by mixing the mobile phase stream exiting the upstream column with a second mobile phase stream with different mobile phase composition ("inline dilution", QC). In another preferred embodiment the mobile phase stream exiting the upstream column is mixed with fresh feed solution.

In a preferred embodiment, in the disconnected configuration feed mixture is applied to one of the columns and in another preferred embodiment the column that has been loaded with feed mixture is washed after the load in order to remove compounds which are not of interest. In another preferred embodiment the second column is washed in order to remove compounds which are not of interest. In an even more preferred embodiment, the column that has been initially washed is equilibrated so that compounds of interest can adsorb on the stationary phase.

In a preferred embodiment, in the accumulation phase, in the disconnected configuration, the feed mixture is supplied at position 2 into the downstream column and in parallel the upstream column at position 4 is cleaned. Even more preferably, the column at position 2 is washed after having been loaded with feed, keeping the compounds of interest inside the column. In another preferred embodiment, a modifier gradient is applied to the column at position 2 following the washing step.

Even more preferably, the column at position 4 is equilibrated after having been cleaned In another preferred embodiment, feed solution is applied to the column at position 4 after the column has been equilibrated.

After having completed the tasks at positions 2 and 4 the columns are switched such that the upstream column becomes the downstream column and vice versa, i.e. the column from position 4 switches to position 1, the column from position 2 switches to position 3, and the columns are interconnected such that the outlet of the upstream column is connected to the inlet of the downstream column. During the interconnected phase, a mobile phase stream is supplied to the upstream column at position 3, washing out the compounds of interest from said column. The stream exiting the upstream column is modified in composition such that the compounds of interest are capable of adsorbing after having been washed into the downstream column at position 1.

After the compounds of interest have been washed into the downstream column at position 1, the columns are disconnected and the downstream column is switched to position 2 and the upstream column is switched to position 4 and the tasks of the disconnected state are repeated.

In a further preferred embodiment of the process, the accumulation phase of the process is run over multiple switches M until satisfactory enrichment of the compounds of interest inside the columns has been achieved.

In a preferred embodiment of the process, the accumulation phase is followed by a separation phase, i.e. N>0, which is run over at least one switch and comprises the steps described above for the accumulation phase except for that no feed solution is loaded. Instead of the feed either washing solution or no mobile phase at all is supplied.

In yet another preferred embodiment, the flow rates, mobile phase compositions and phase durations are different in the separation phase in order to allow for optimal removal of compounds which are not of interest.

In a preferred embodiment, the compounds of interest are isolated in a final elution phase from the column that contains the compounds of interest. In another preferred embodiment the final elution phase includes a buffer or solvent gradient, more preferably a linear solvent gradient mixed from at least two solvents with different elution strengths. In another preferred embodiment, the process uses a constant modifier condition (isocratic conditions). In another preferred embodiment one or more column washing steps are included in the final elution phase.

In another preferred embodiment, prior to isolation, the compounds of interest are washed out of the respective column and through the second column, which has previously been cleaned, equilibrated and interconnected with the column that contains the compounds of interest.

Preferably the column switching is realized by altering the flow path by means of valves without physically moving the columns.

In a preferred embodiment, the process is monitored online completely or partially by at least one of the following measurement techniques: UV absorption, visible light absorption, light scattering, conductivity, pH, fluorescence, mass spectrometry (MS), infrared spectroscopy (IR). In another preferred embodiment the effluent is fractionated during the final elution phase, and even more preferably, the process is completely or partially monitored online and fractionated during the final elution phase for further analysis and/or processing.

In another preferred embodiment, supercritical fluids or mixtures containing supercritical fluids are used as mobile phases.

In a further preferred embodiment the process is used as part of a method serving one of the following purposes: discovery of compounds of interest in a multicompound mixture including but not limited to the discovery of leads in pharmaceutical development; enrichment and isolation of compounds of interest such as trace compounds in multicompound mixtures including but not limited to the enrichment and isolation of product-related impurities or isoforms in pharmaceutical characterization and impurity profiling.

In a preferred embodiment the process is used as part of a method serving one of the abovementioned purposes and comprises further processing steps such as sample preparation for chromatography and fraction analysis including but not limited to analysis techniques such as high performance liquid chromatography (HPLC), gas chromatography (GC), photometry, mass spectrometry (MS), infrared spectroscopy (IR), fluorometry, Raman spectroscopy, nuclear magnetic resonance (NMR), differential scanning calorimetry (DSC), differential scanning fluorometry, circular dichroism (CD), capillary electrophoresis (CE), gel electrophoresis (SDS-PAGE), iso-electric focusing (IEF), Immunosorbent assay (ELISA), western blot and related techniques and combinations thereof and analysis methods such as peptide mapping and gene mapping and in general matching against databases to identify the compounds of interest.

Further embodiments of the invention are laid down in the dependent claims.

BRIEF DESCRIPTION OF THE DRAWINGS

Preferred embodiments of the invention are described in the following with reference to the drawings, which are for the purpose of illustrating the present preferred embodiments of the invention and not for the purpose of limiting the same. In the drawings.

FIG. 8 shows the isolation of W-product-related impurities by single column batch chromatography (comparative example 1);

DESCRIPTION OF PREFERRED EMBODIMENTS

Example 1

Figure 1:
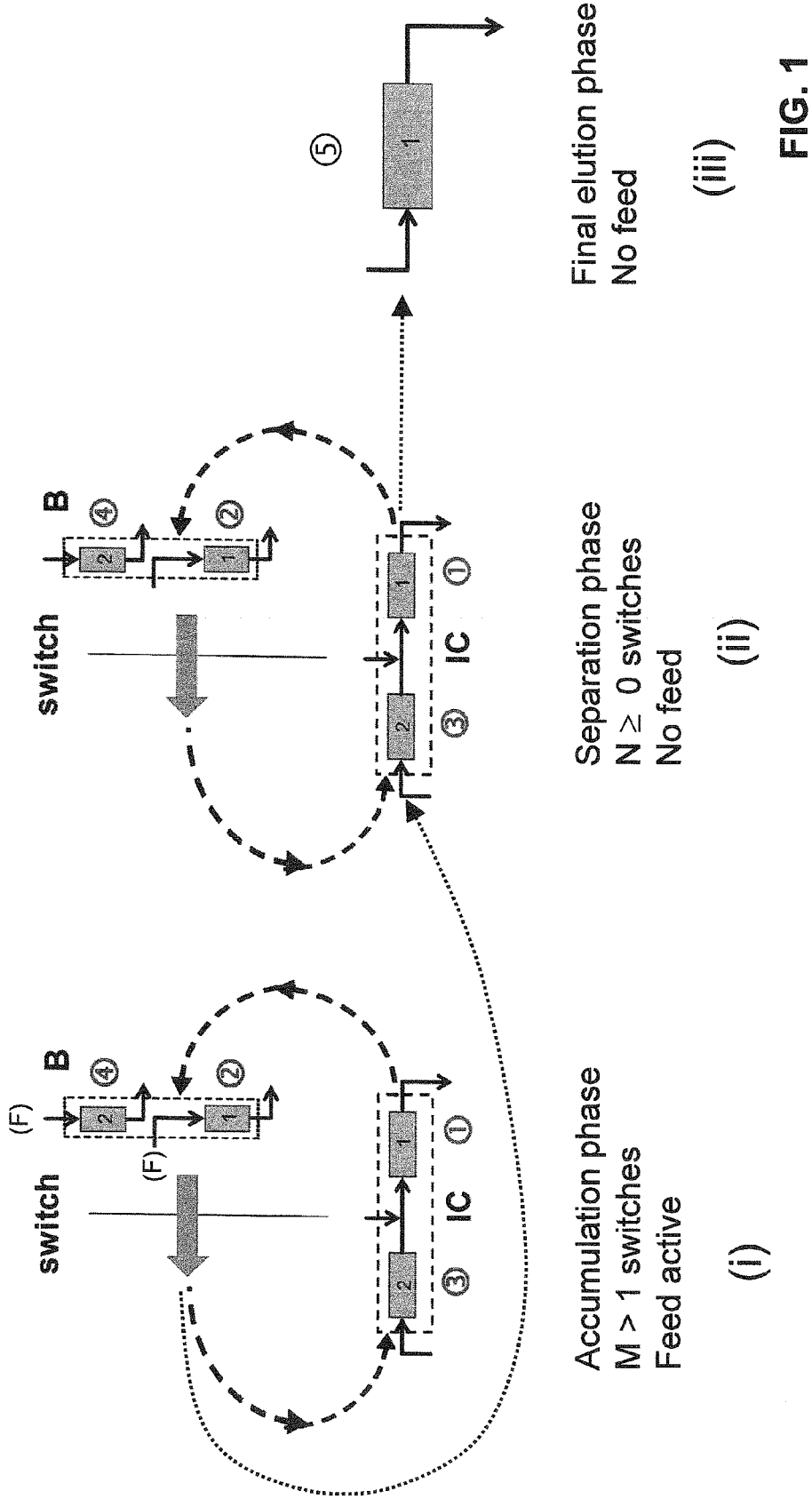
FIG. 1 shows a schematic flow sheet of the proposed process including: (i) cyclic accumulation phase, (ii) optional separation phase and (iii) final elution phase; the grey rectangles indicate the columns or groups of columns, respectively, and the numbers in the circles indicate the column positions; the dashed rectangles indicate the interconnected and disconnected column configurations, respectively; the thick dashed curved arrows indicate the direction of column switching within the cyclic accumulation/cyclic separation phase; the solid arrows indicate liquid flows; the dotted arrows mark the entrance of the columns into the next phase (from the cyclic accumulation phase into the cyclic separation phase, and from the cyclic separation phase into to final elution phase); the solid vertical line and the thick grey arrow indicate the column position change where the upstream column becomes the downstream column and vice versa; (F) indicates the potential feed positions.
Figure 2:
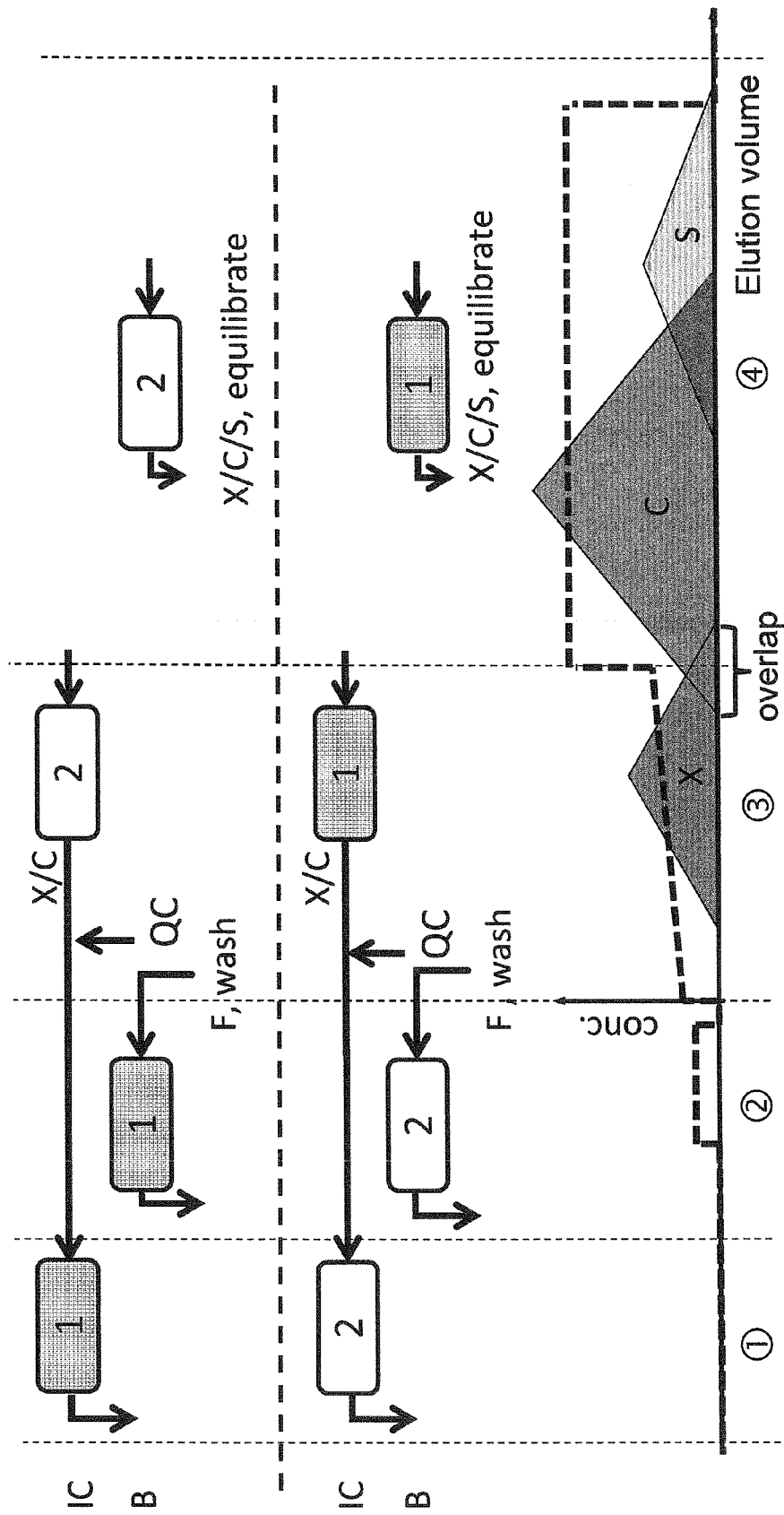
FIG. 2 shows a general process flow sheet showing the cyclic accumulation phase for enrichment of compounds of interest which include the most weakly adsorbing compounds, i.e. the compounds of interest are early eluting (X=W); the upper part of the Figure shows the four sections of the process using two columns (1, 2) corresponding to four tasks, wherein the section/task numbers are indicated below the x-axis (elution volume axis); solid arrows indicate flows of mobile phase; IC indicates interconnected state, where the outlet of the upstream column is directly connected to the inlet of the downstream column; B indicates batch state, where each of the columns is run in batch mode and where they are not connected with each other; the column switch (where the downstream column becomes the upstream column and vice versa) is indicated by the horizontal dashed line in the upper part of the figure; capital letters X, C, S, indicate the compounds to be separated, wherein X represents the compounds of interest; the lower part of the figure shows schematically the chromatogram at the outlet of the column in the respective section, elution volume running from left to right; the vertical dashed lines indicate the section borders which are important for process operating parameter determination (flow rates, gradient concentrations)
Figure 3:
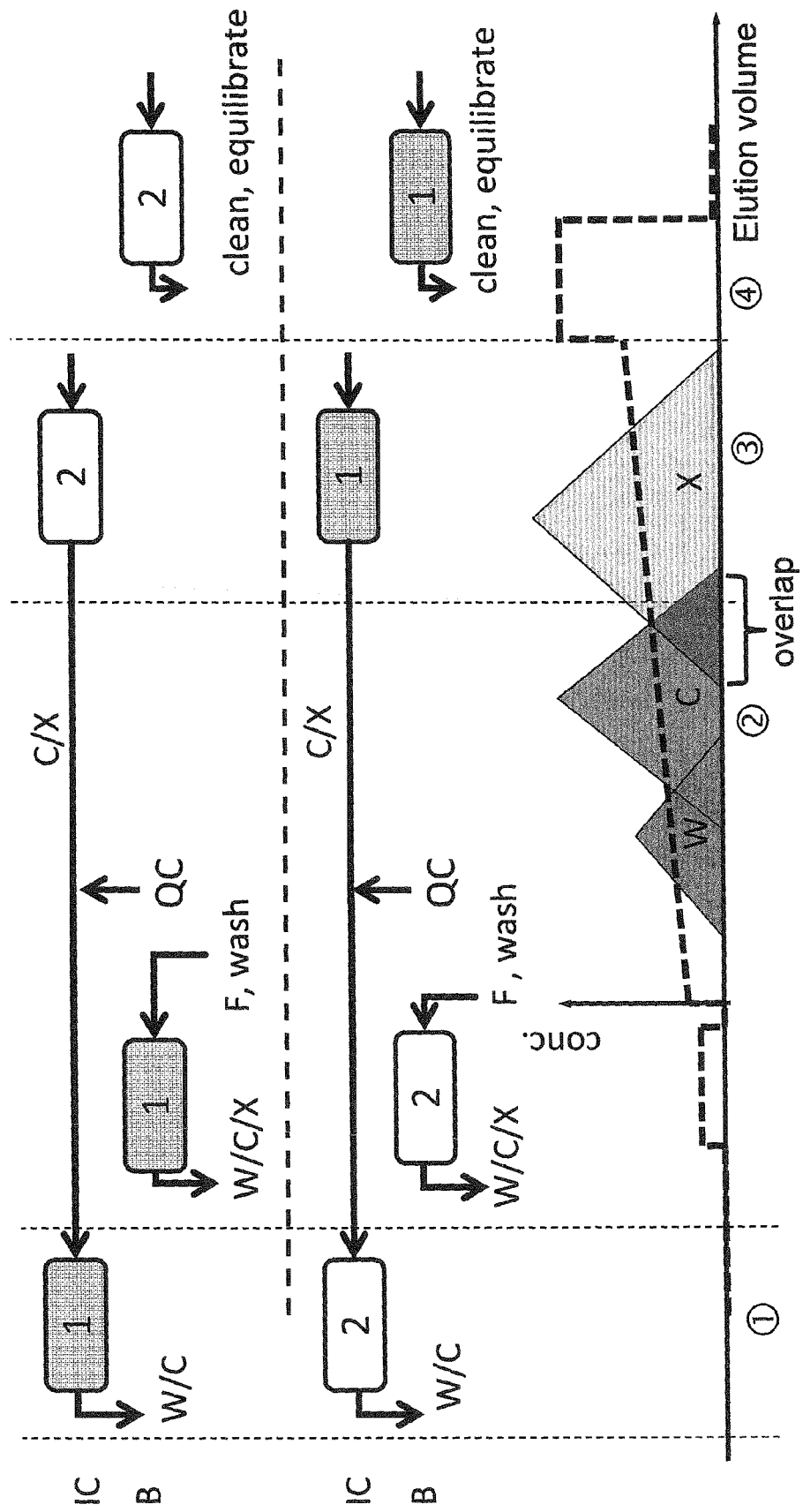
FIG. 3 shows a general process flow sheet showing the cyclic accumulation phase for enrichment of compounds of interest which include the most strongly adsorbing compounds, i.e. the compounds of interest are late eluting (X=S); W, C indicate compounds that are not of interest, further description see FIG. 1.
Figure 4:
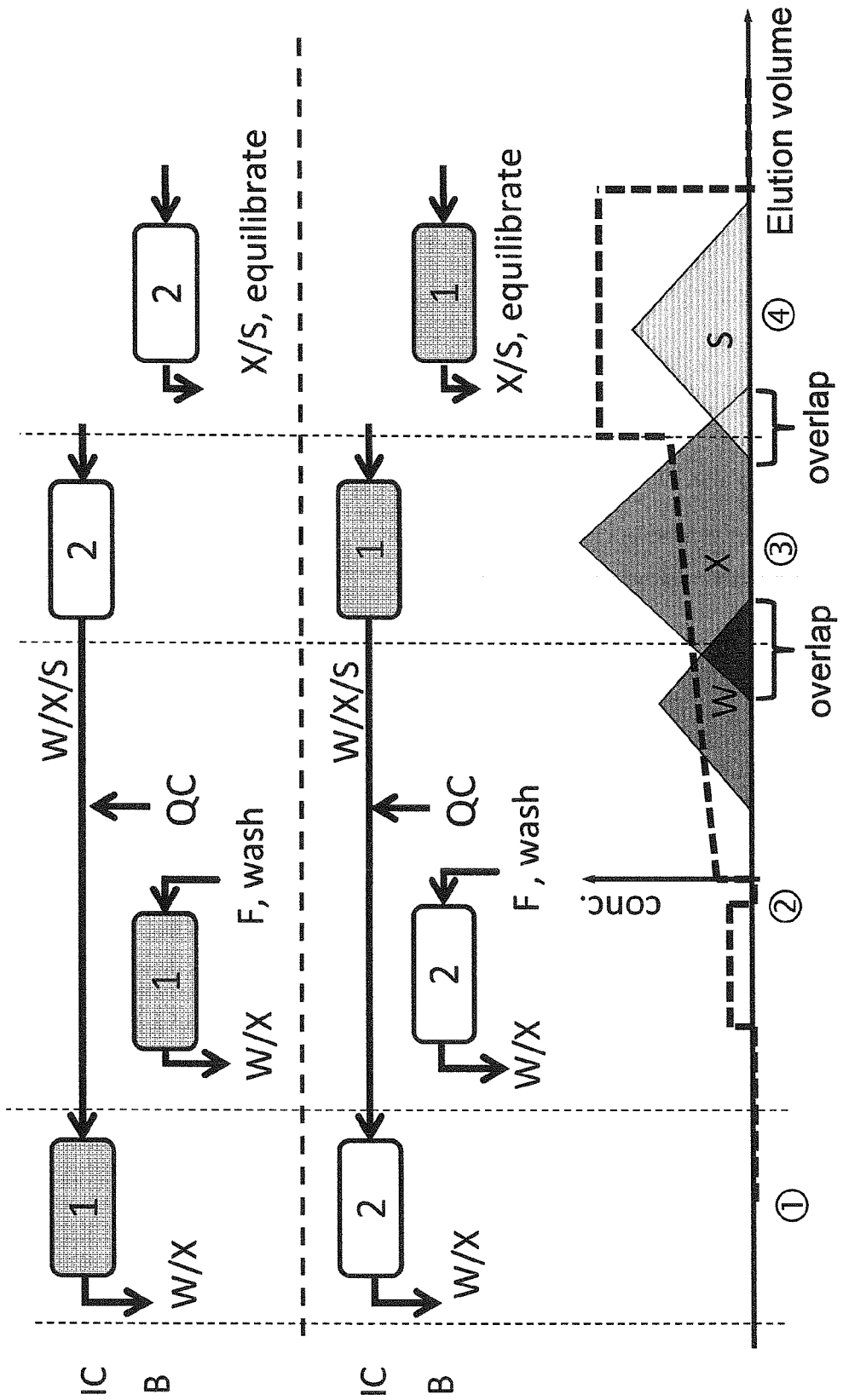
FIG. 4 shows a general process flow sheet showing the cyclic accumulation phase and enrichment of compounds of interest which include intermediately adsorbing compounds X, which are flanked by early eluting impurities (W) and late early eluting impurities (S), i.e. the compounds of interest are center-eluting (X=C); further description see FIG. 1.
Figure 5:
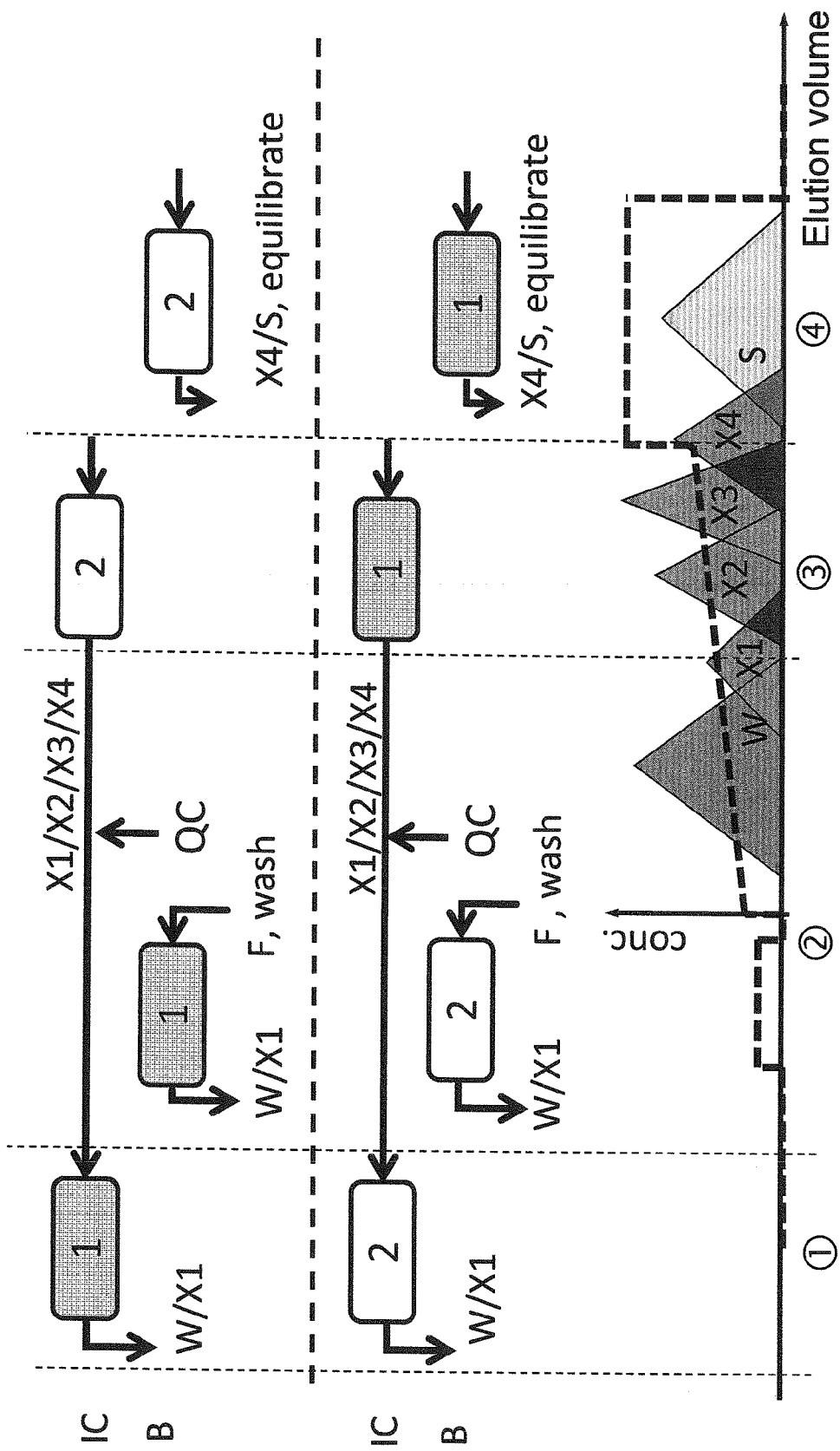
FIG. 5 shows a general process flow sheet showing the cyclic accumulation phase and enrichment of compounds of interest which include intermediately adsorbing compounds X1-X4, which are flanked by early eluting impurities (W) and late early eluting impurities (S), i.e. the compounds of interest are center-eluting (X=C), and where there are multiple compounds in the center; further description see FIG. 1.

Product-Related Impurity Isolation of Fibrinopeptide A, Early Eluting X Compounds The described process was used to isolate the weakly adsorbing product-related side compounds of Fibrinopeptide A for further characterization. The Fibrinopeptide A had been produced by chemical synthesis which generally leads to the formation of product-related side compounds. The side compounds represent potential health risks and have to be removed in the chromatographic purification of the pharmaceutical. Characterization of the side compounds allow for evaluation of the health risk and improvement of the chemical synthesis in order to reduce formation of the side compounds.

The feed was prepared by weight. In order to obtain approximately 110 mL of feed solution, 0.45 g of crude Fibrinopeptide A was dissolved in a mixture of 92.6 g de-ionized water, 22.5 g Acetonitrile, and 3.0 g acetic acid. The concentration of the crude material was 3.6 g/L. The feed contained approximately 1.1 g/L Fibrinopeptide A (feed purity 30%). Kromasil C18-100-10 was used as preparative and analytical stationary phase. The column size was 4.6 mm i.D.×100 mm L in both cases. Analytics were performed using an Agilent HP 1100 series (Agilent, Santa Clara, Calif., USA). For the analytics, a flow rate of 0.5 mL/min was used and a gradient from 0-100% solvent B was run within 45 min. The injection volume was 50 µL (feed) and 100 µL (fractions), respectively. The solvents were the same for analytical and preparative experiments and were prepared by weight. 1 L of solvent A contained 903.6 g of de-ionized water, 48.2 g of Acetonitrile, and 0.9 g of TFA. 1 L of solvent B contained 486.7 g of de-ionized water, 400.0 g of Acetonitrile, and 0.5 g of TFA.

The reported process was carried out using Contichrom® Lab-10 equipment from ChromaCon, Zurich, Switzerland. The UV-absorption was monitored at 280 nm, and the temperature was 25° C. for both analytics and preparative runs. UV-detectors were mounted at the outlet of each column.

The process operating parameters are reported in Table 1.

The cycle duration was 98.2 min and the cyclic accumulation phase of the novel process was 8 cycles. The separation phase was omitted. The final elution phase for the elution of the accumulated W-compounds and the isolation by fractionation at 1 min per fraction and had a duration of 80.3 min. Thus the duration of the complete run was 8×98.2 min+80.3 min=866 min=14.4 h.

The load was 4 mL of sample per cycle, which corresponds to 14.4 mg crude material per cycle (feed concentration 3.6 mg/mL crude). Thus, during the entire experiment 8×14.4 mg/(2×1.66 mL)=34.7 mg of crude material per mL of column volume was loaded. The load per time and total column volume was 2.4 g/L/h.

Figure 6:
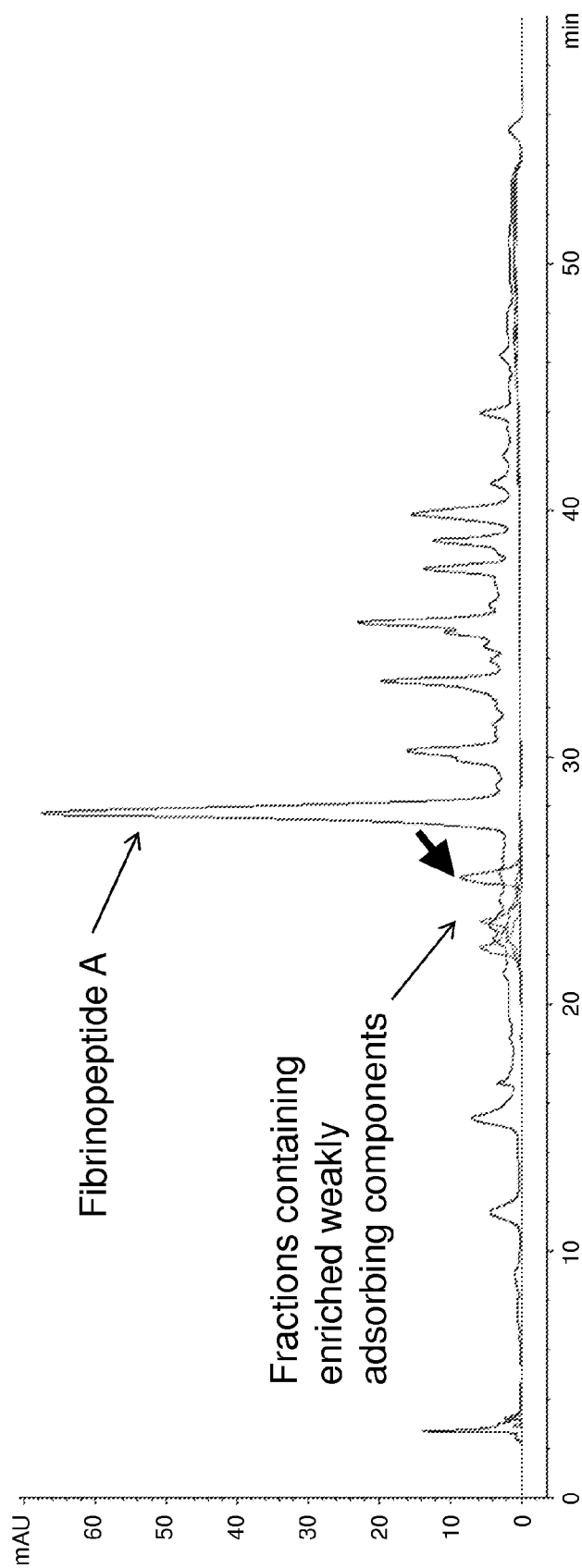
FIG. 6 FIG. 8 FIG. 6 shows the isolation of W-product-related impurities of Fibrinopeptide A using the novel process: Overlay of analytical chromatograms and chromatograms of purest fractions obtained from a final gradient elution.
Figure 7:
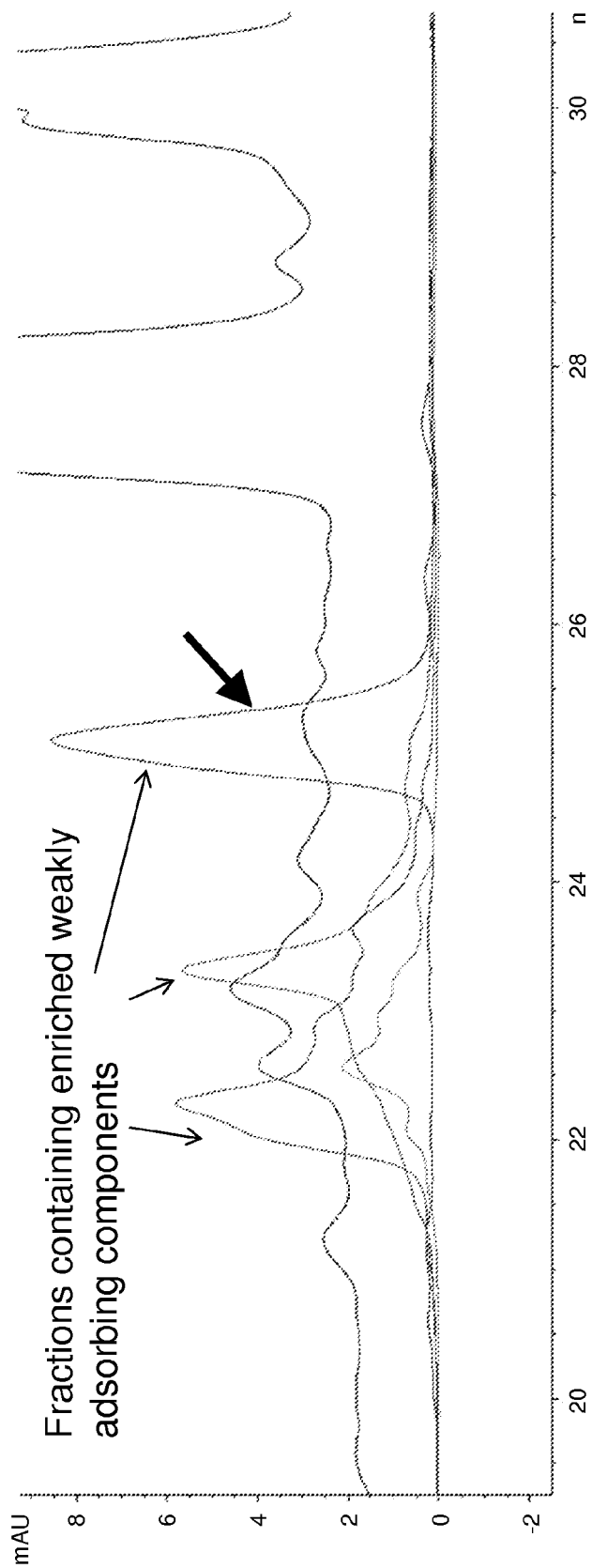
FIG. 7 shows the isolation of W-product-related impurities using the novel process: Zoom of FIG. 6.

The fractions obtained from the final elution phase were analyzed using the chromatographic analytics. An overlay of the analytical chromatograms of a feed sample and fractions containing enriched and isolated weakly adsorbing side compounds of Fibrinopeptide A is shown in FIG. 6. A zoom of the chromatogram is provided in FIG. 7. The chromatograms show significant enrichment and high purity of the side-compounds. A compound of particular interest is indicated with an arrow in FIG. 7. This compound could be obtained with a purity of 80% in one of the fractions of the final elution phase. The concentration of the compound in this fraction was approximately 8-fold larger than the concentration of the compound in the feed mixture.

TABLE 1

Operating parameters of the novel process for isolation of weakly adsorbing, early eluting side compounds of Fibrinopeptide A

| | | | gradient [% B] | |
|---|---|---|---|---|
| Cyclic accumulation phase | | | start | end |
| Interconnected state (IC), tasks 1 and 3 | | | | |
| duration | [min] | 23.00 | | |
| flow rate in upstream column (pos 3) | [mL/min] | 0.49 | 20 | 42.5 |
| flow rate QC | [mL/min] | 0.50 | 0 | 0 |
| Disconnected state (B), task 4 (clean) | | | | |
| duration | [min] | 8.00 | | |
| flow rate | [mL/min] | 0.49 | 100 | 100 |
| Disconnected state (B), task 4 (equil) | | | | |
| duration | [min] | 10.50 | | |
| flow rate | [mL/min] | 0.49 | 0 | 0 |
| Disconnected state (B), task 2 (feed) | | | | |
| duration | [min] | 8.00 | | |
| flow rate (feed) | [mL/min] | 0.50 | feed | feed |
| Disconnected state (B), task 2 (wash) | | | | |
| duration | [min] | 10.50 | | |
| flow rate | [mL/min] | 0.43 | 20 | 20 |
| Final gradient elution phase | | | | |
| gradient duration | [min] | 60 | | |
| gradient flow rate | [mL/min] | 0.50 | 20 | 80 |

Comparative Example 1

Product-Related Impurity Isolation of Fibrinopeptide a (Early Eluting X Compounds) by Single Column Batch Chromatography A single column batch reference experiment was run with the parameters reported in Table 2. The duration of this experiment was 129 min=2.2 h.

In the batch reference experiment, 1.375 mL of sample was loaded corresponding to a load of 3 mg crude per mL of column volume. The load per time and total column volume was 1.4 g/L/h. Thus the load per time and total column volume was in the same order of magnitude for the process described in example 1 and in this example. The gradient operated in the single column batch reference had the same slope as the final elution phase gradient in the process reported in example 1, and the flow rate was almost the same. The reference run was fractionated with a rate of 1 min/fraction.

TABLE 2

Operating parameters of single column batch reference run

| | | | gradient [% B] | |
|---|---|---|---|---|
| task description | pump parameters | | start | end |
| equilibration | [min] | 15 | | |
| | [mL/min] | 0.5 | 0 | 0 |
| feed | [min] | 2.75 | | |
| | [mL/min] | 0.5 | feed | feed |
| wash | [min] | 10 | | |
| | [mL/min] | 0.5 | 0 | 0 |
| gradient elution | [min] | 60 | | |
| | [mL/min] | 0.5 | 20 | 80 |
| hold | [min] | 10 | | |
| | [mL/min] | 0.5 | 80 | 80 |
| CIP | [min] | 15 | | |
| | [mL/min] | 0.5 | 100 | 100 |
| re-equil | [min] | 15 | | |
| | [mL/min] | 0.5 | 0 | 0 |

Figure 8:
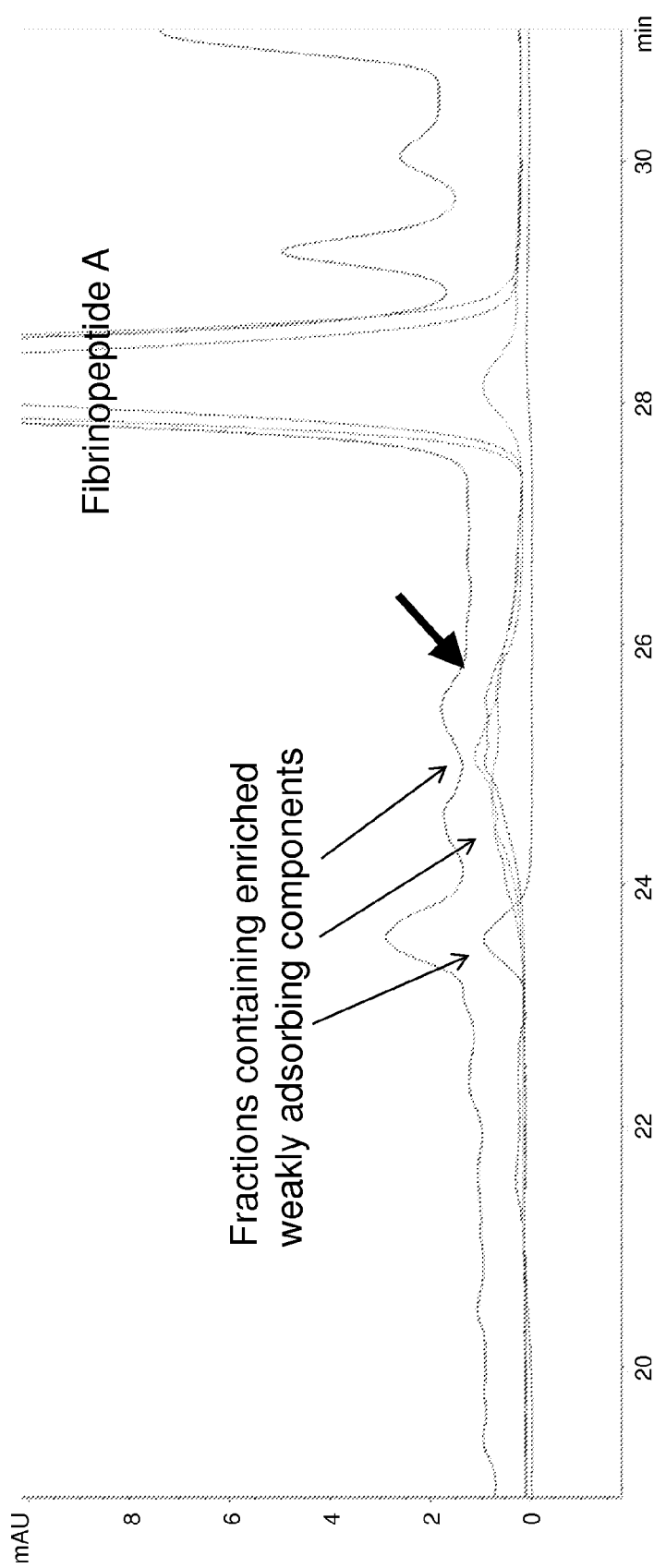

An overlay of the analytical chromatograms of different fractions showing the purest fractions containing W impurities obtained from the single column batch reference run is provided in FIG. 8. It can be noticed that 1. With the single column batch process it was not possible to obtain a single W-product-related compound with high purity.
2. The product-related compounds are far less concentrated than the ones obtained using the novel process The difference between the batch and the novel process is particularly striking in the case of the compound that is indicated with an arrow in FIG. 7 (example 1) and FIG. 8 (comparative example). While with the presented process (example 1) a fraction of >80% purity of this product-related impurity is obtained, the fraction with the highest purity isolated by conventional batch chromatography has <20% purity. The low purities obtained with single column chromatography are due to the large amounts of main compound (Fibrinopeptide A) present in the samples. The concentration of the compound of interest, obtained by single column chromatography is 6-7-fold lower than the concentration obtained using the novel process. Thus, by pooling and concentrating W-fractions containing the compound of interest from 6-7 batch runs one could obtain the same compound of interest concentration as with the novel process but not the same purity. Note that, if the process described in example 1 would have been operated for a longer time period, the enrichment could have been carried on even further.

Example 2

Product-Related Impurity Isolation of Fibrinopeptide A, Late Eluting X Compounds The described process was used to enrich and isolate the strongly adsorbing product-related side compounds of Fibrinopeptide A using the same materials as described in example 1. Only the operating parameters were different and are reported in Table 3. The cyclic accumulation phase of the process was run for five cycles. The separation phase was operated for one cycle. During the final elution phase, fractions were taken at 1 min/fraction.

TABLE 3

Operating parameters of the novel process for isolation of strongly adsorbing, late eluting side compounds of Fibrinopeptide A

| | | | gradient [% B] | |
|---|---|---|---|---|
| Cyclic accumulation phase, cyclic separation phase | | | start | end |
| Interconnected state (IC), tasks 1 and 3 | | | | |
| duration | [min] | 51.50 | n.a. | n.a. |
| flow rate in upstream column (pos 3) | [mL/min] | 0.38 | 40.8 | 79.8 |
| flow rate QC | [mL/min] | 0.62 | 0 | 0 |
| Disconnected state (B), task 4 (clean) | | | | |
| duration | [min] | 10.50 | | |
| flow rate | [mL/min] | 0.49 | 100 | 100 |
| Disconnected state (B), task 4 (equil) | | | | |
| duration | [min] | 10.50 | | |
| flow rate | [mL/min] | 0.49 | 0 | 0 |
| Disconnected state (B), task 2 (feed) | | | | |
| duration | [min] | 5.00 | | |
| flow rate (feed) | ([mL/min]) | 0.42* | feed | feed |
| Disconnected state (B), task 2 (wash) | | | | |
| duration | [min] | 16.00 | | |
| flow rate | [mL/min] | 0.43 | 40.8 | 40.8 |
| Final gradient elution phase | | | | |
| gradient duration | [min] | 90 | | |
| gradient flow rate | [mL/min] | 0.50 | 40.8 | 80 |

*feed flow rate is zero in cyclic separation phase

Figure 9:
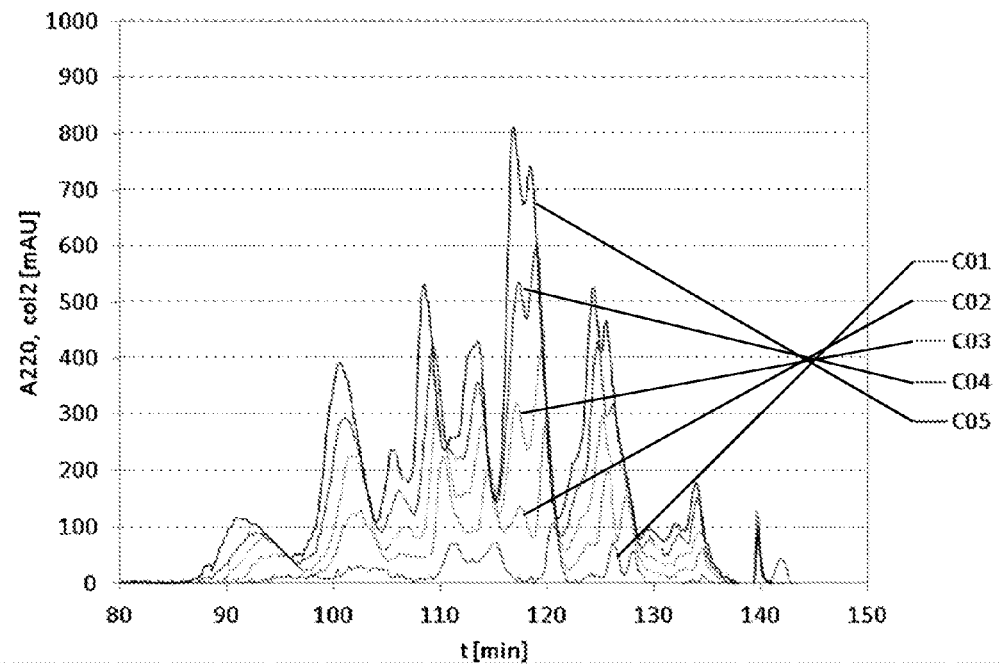
FIG. 9 shows an overlay of chromatograms recorded during the interconnected state of the novel process by the UV detector located in between the two columns ("internal profiles"); the switch duration was 77.5 min.
Figure 10:
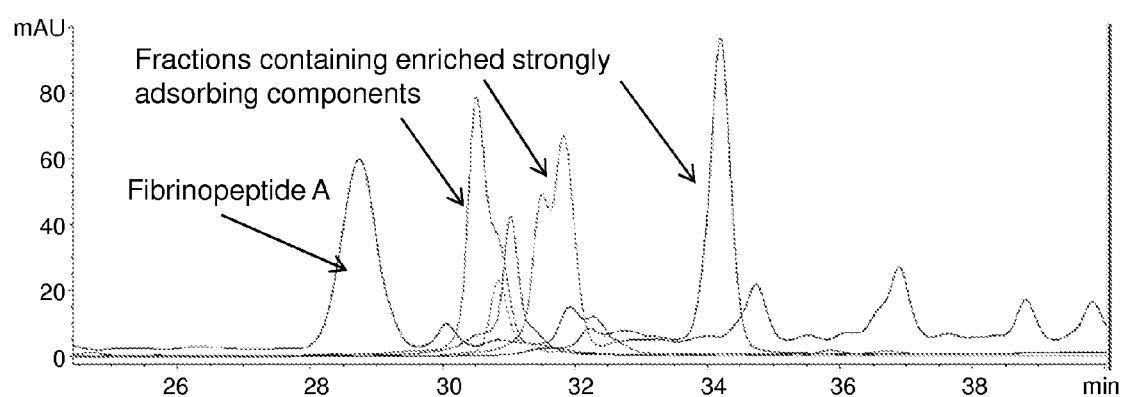
FIG. 10 shows the isolation of S-product-related impurities using the novel process: Overlay of analytical chromatograms and chromatograms of purest fractions obtained from a final gradient elution from the Contichrom® unit; injection volumes: feed: 50 µL, side-compound fractions: 100 µL.

The chromatograms, recorded by the UV detector located on one of the column outlets during the interconnected state IC show the accumulation of the strongly adsorbing X compounds due to the internal recycling (FIG. 9).

The samples obtained during in the final elution phase of the process were analyzed offline using HPLC. An overlay of the feed chromatogram and chromatograms of fractions with the highest purities of single product-related impurities are shown in Figure (the purity is defined as the ratio between the main peak area and the total peak area). It is difficult to assign the peaks of the product-related impurities fractions to the peaks of the feed chromatogram in the analytical chromatograms, and additional analytics such as mass spectrometry would be required to unambiguously identify specific compounds. However it can be clearly seen that strongly adsorbing compounds were obtained with high concentration and purity.

Example 3

Fatty Acid Ethyl Ester Purification, Intermediately Eluting X Compounds

The described process was used to enrich and isolate fatty acid ethyl ester species. Thereby certain fatty acid ethyl ester species that were previously close to the limit of detection were increased in concentration so that a clear signal in the analytics was obtained.

In comparison, a single column batch gradient experiment was carried out using the same time-specific load as in the process at a flow rate of 3 mL/min and with 0.25 min fractionation intervals. In the batch run, the main compound, eicosapentaeonic acid ethyl ester (EPA-EE) elutes first and the secondary compound docosahexaeonic acid ethyl ester (DHA-EE) elutes later. A number of other fatty acid ethyl esters are eluting in between. In the batch chromatogram the peaks cannot be distinguished, however, from the fractionation and offline analysis of the fractions using gas chromatography, the positions, concentrations and purities of the main fatty acid ethyl ester species could be identified. In this case, the concentrations and purities of fatty acid ethyl ester species X, eluting in between EPA-EE and DHA-EE, were of particular interest.

Using the information on peak positions and concentrations from the single column batch experiment, the novel process was designed and operated for the enrichment and isolation of the fatty acid ethyl esters eluting in between EPA-EE and DHA-EE. The novel process was operated with two 6 mm i.D.×150 mm L C18 silica reversed phase columns with 15 um particles and 120 A pore size and aqueous ethanol solution as solvent under isocratic conditions. The cyclic accumulation phase was 10 cycles, the cyclic separation phase was omitted and the final elution was carried out through both columns after the column that did not contain the compounds of interest had been cleaned and re-equilibrated. The fractionation was done at 0.5 min per fraction at a flow rate of 2 mL/min.

Figure 11:
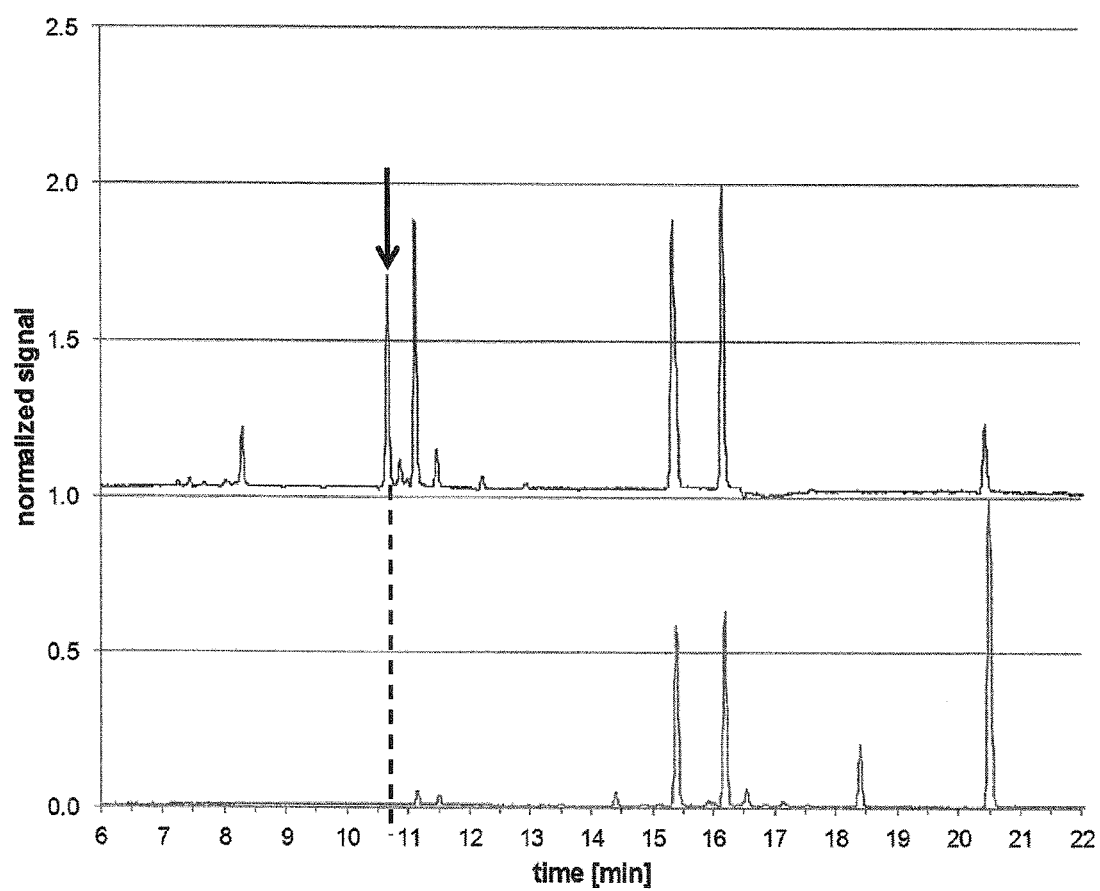
FIG. 11 shows an overlay of analytical GC chromatograms of a fraction containing intermediate fatty acid ethyl esters; peaks normalized for highest peak; upper curve: novel process, lower curve: batch process; the newly discovered compound is indicated with an arrow.
Figure 12:
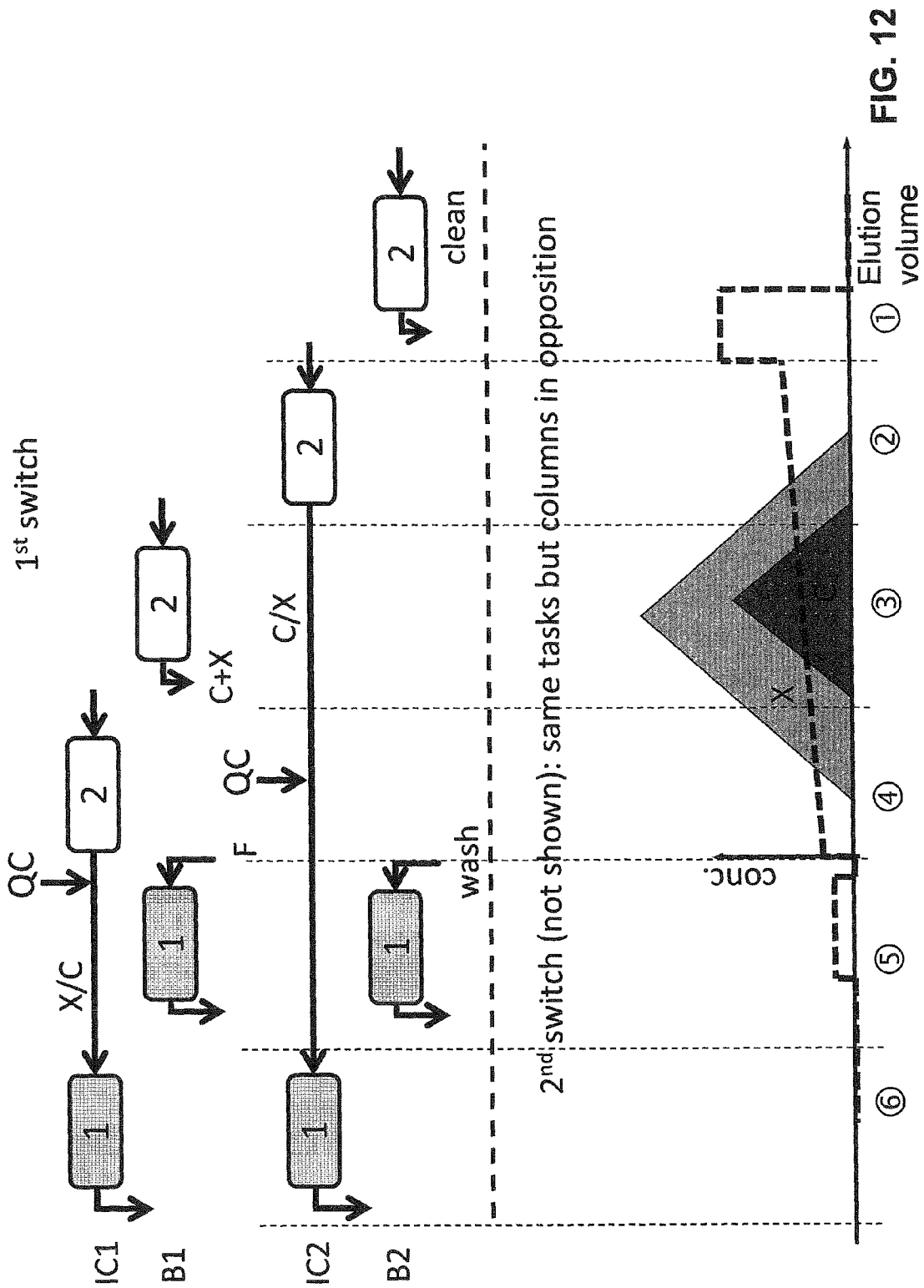
FIG. 12 shows a general process flow sheet showing the cyclic accumulation phase and enrichment for a situation where the compounds of interest X1, X2 are early and late eluting, embracing a center eluting compound C which is not of interest; further description see FIG. 1.

The fractions from both processes were analyzed using gas chromatography (GC). A comparison of two GC chromatograms showing the purest fractions with respect to a fraction of the intermediate fatty acid ethyl esters X is shown in FIG. 11 (upper part: results from novel process, lower part: results from batch process). In the chromatogram of one of the fractions obtained with the novel process, a compound was discovered (indicated with an arrow in FIG. 11) which was not clearly detectable in the feed chromatogram (not shown). The compound is present with a purity of 15.2% and a concentration far above the detection limit Re-analyzing the feed chromatogram, it was found that this compound was present in the feed solution with a purity of 0.05%+/−0.02% with a concentration verging on the detection limit of the method. Also in the case of the single column run, the compound concentration was close to the detection limit and the purity was only 0.04+/−0.02%.

The maximum concentrations obtained in any of the fractions for the abovementioned compound is 3.1 relative mass units in the feed mixture, 0.5 relative mass units in the highest concentration fraction of the single column batch process and 26.8 relative mass units in the high purity fraction of the novel process. The mass balance for the compound in the novel process is 7.8%.

Summarizing, with the novel process it was possible to increase the concentration of the compound of interest by approximately a factor of 9 and to increase the purity by >300-fold over the feed concentration and purity, respectively. With the single column batch process no improvement in terms of concentration and purity over the feed properties could be obtained. The superior enrichment and isolation capabilities of the novel process significantly facilitated the identification of the newly discovered compound whose existence was previously not clear.

LIST OF REFERENCE SIGNS

| | |
|---|---|
| X | compound of interest |
| X1, X2, X3, X4 | compounds of interest |
| S | strongly adsorbing compound, not of interest |
| W | weakly adsorbing compound, not of interest |

-continued

LIST OF REFERENCE SIGNS

| | |
|---|---|
| C | intermediate adsorbing compound, not of interest |
| M | number of cycles in the accumulation phase |
| N | number of cycles in the separation phase |
| B | disconnected state (batch state) |
| IC | interconnected state |
| F | feed, input of the mixture to be treated |
| QC | in-line dilution |

The invention claimed is:

1. A chromatographic process for enrichment of at least one compound of interest from a mixture comprising said at least one compound of interest as well as at least one further compound, which is not of interest, using at least two chromatographic columns comprising a first and a second column, or a group of columns, each column having an inlet and an outlet, wherein said process at least involves a sequence of the following steps:
(i) a cyclic accumulation phase,
wherein the at least two chromatographic columns are alternatingly or synchronously operated in a first pairing of two phases of an accumulation cycle, comprising an interconnected phase followed by a disconnected phase,
wherein after said first pairing of two phases forming the accumulation cycle, the first and second column or group of columns exchange positions to undergo the a next pairing of two phases comprising said interconnected and disconnected phases of the cyclic accumulation phase;
wherein at least one of said columns or group of columns in at least one of said interconnected phases or disconnected phases is fed with said mixture via its inlet;
wherein in neither of said interconnected phases or disconnected phases is said at least one compound of interest extracted in isolated form via an outlet of any of said at least two chromatographic columns; and
wherein said two phases of the cyclic accumulation phase are carried out sequentially M times with M >1;
(ii) a cyclic separation phase,
wherein the at least two chromatographic columns are alternatingly or synchronously operated in a first pairing of two phases of a separation cycle, comprising an interconnected phase followed by a disconnected phase,
wherein after said first pairing of two phases forming the separation cycle, the first and second column or group of columns exchange positions to undergo a next pairing of two phases comprising said interconnected and disconnected phases of the cyclic separation phase;
wherein in neither of said interconnected phases or disconnected phases is said at least one compound of interest extracted in isolated form via an outlet of any of said at least one two chromatographic columns; and
wherein via the outlet of at least one of said columns or group of columns the at least one further compound, which is not of interest, is discharged from the system;
wherein said two phases of the cyclic separation phase are carried out sequentially N times with N ≥0; and (iii) an elution phase, in which from the column or group of columns, which at an end of phase (i) or, in case of N>0 at an end of phase (ii) contains the at least one compound of interest, said at least one compound of interest is extracted via the outlet.

2. A chromatographic process according to claim 1, wherein said process at least involves a sequence of the following steps:
(i) said cyclic accumulation phase,
wherein the at least two chromatographic columns are alternatingly operated in said first pairing of two phases of said accumulation cycle, comprising:
said interconnected phase of said cyclic accumulation phase in which an outlet of a first upstream column or group of columns is fluidly connected to an inlet of a second downstream column or group of columns such as to transfer at least a fraction of the compound of interest from the upstream column or group of columns to the downstream column or group of columns, followed by
said disconnected phase of said cyclic accumulation phase, in which the first upstream column or group of columns and the second downstream column or group of columns are not fluidly connected, wherein at least one of the columns or group of columns is fed with said mixture via its inlet, and wherein via the outlet of at least one of said first and/or second column or group of columns the at least one further compound, which is not of interest, is discharged from the system;
wherein after said first pairing of two phases forming said accumulation cycle, the first and second column or group of columns exchange positions to undergo next interconnected and disconnected phases to form a full accumulation cycle; and
wherein said two phases of the cyclic accumulation phase are carried out sequentially M times with M >1;
(ii) said cyclic separation phase, in which
wherein the at least two chromatographic columns are alternatingly operated in said first pairing of two phases of the separation cycle, comprising:
said interconnected phase of said cyclic separation phase, in which an outlet of a first upstream column or group of columns is fluidly connected to an inlet of a second downstream column or group of columns such as to transfer at least a fraction of the compound of interest from the upstream column or group of columns to the downstream column or group of columns; followed by
said disconnected phase of said cyclic separation phase, in which the first upstream column or group of columns and the second downstream column or group of columns are not fluidly connected, wherein none of the columns or group of columns is fed with mixture via its inlet, but wherein via the outlet of at least one of said first and/or second column or group of columns the at least one further compound, which is not of interest, is discharged from the system;
wherein after said first pairing of two phases the first column or group of columns and the second column or group of columns exchange positions to undergo a next pairing of two phases comprising said interconnected and disconnected phases to form a full separation cycle;
wherein said two phases of the cyclic separation phase are carried out sequentially N times with N ≥0; and
(iii) said elution phase, in which from the column or group of columns, which at an end of phase (i) or, in case of N>0 at an end of phase (ii) contains the at least one compound of interest, said at least one compound of interest-is extracted via the outlet.

3. A chromatographic process according to claim 2, wherein in the disconnected phase-of the cyclic accumulation phase (i) the column or group of columns, which in a preceding interconnected phase was the downstream column or group of columns is fed with mixture via its inlet or wherein in the disconnected phase of the cyclic accumulation phase (i) the column or group of columns, which in a preceding interconnected phase was the upstream column or group of columns is fed with mixture via its inlet or the column after having been cleaned and equilibrated.

4. A chromatographic process according to claim 1, wherein in the interconnected phase of the cyclic accumulation phase (i) properties of the stream exiting the upstream column or group of columns are changed.

5. A chromatographic process according to claim 1, wherein in the disconnected phase of the cyclic accumulation phase (i) the column or group of columns, which is fed with the mixture via its inlet, is in a first phase of the disconnected phase fed with the mixture via its inlet, and in a second phase of the disconnected phase is fed with buffer, and/or solvent and/or modifier without the mixture.

6. A chromatographic process according to claim 1, wherein in the elution phase (iii) an eluted compound of interest is subjected to outlet fractionation.

7. A method of using the chromatographic process according to claim 6, wherein the fractionation of the compounds of interest recovered in the final elution phase is subjected to further processing and/or online analysis, which is carried out either manually or automatically.

8. A method of using the chromatographic process according to claim 6, wherein the fractionation of the compounds of interest recovered in the final elution phase is subjected to further processing and/or online analysis, which is carried out either manually or automatically, wherein the further processing includes at least one of the following processes selected from the group consisting of: analysis of the fractions; chromatographic method; mass spectrometry; matching against a database; use of a binding assay; use of a cell based assay.

9. A chromatographic process according to claim 1, wherein in the elution phase (iii) the compound of interest is eluted from a configuration, in which an outlet of a first upstream column or group of columns is fluidly connected to an inlet of a second downstream column or group of columns.

10. A chromatographic process according to claim 1,
where the compound of interest is a weakly adsorbing fraction of a chromatographic elution profile, wherein in the disconnected phase of the cyclic accumulation phase (i), and in case of N>0 also of the cyclic separation phase (ii), the column or group of columns which is not fed with mixture is operated so as to elute the at least one further compound, which is not of interest,
and/or where the compound of interest is a strongly adsorbing fraction of the chromatographic elution profile, in the disconnected phase of the cyclic accumulation phase (i), and in case of N>0 also of the cyclic separation phase (ii), the column or group of columns which is not fed with mixture is operated so as to be equilibrated, and the column or group of columns which is fed with mixture is operated such as to elute an at least one further weaker adsorbing compound, which is not of interest or to wash out the at least one further weaker adsorbing compound in the subsequent interconnected phase;
wherein the degree, to which next to the least one further compound, which is not of interest, also a part of the compound of interest is eluted, is adapted as a function of a desired enrichment and/or absolute concentration of the compound of interest in an eluate of the elution phase (iii).

11. A chromatographic process to according claim 1, wherein gases or supercritical fluids are used as solvents, and/or wherein a phase comprises a change of a mobile phase composition over time.

12. A chromatographic process to according claim 1, wherein M >2.

13. A chromatographic process to according to claim 1, wherein N >0.

14. A chromatographic process to according to claim 1, wherein in the cyclic accumulation phase (i) in only every second disconnected phase a column is fed with mixture via its inlet, and wherein only after four phases the first and second column or group of columns exchange positions to undergo the next interconnected and disconnected phases of the cyclic accumulation phase.

15. A method of using the chromatographic process according to claim 1, to enrich, isolate, or discover compounds of interest.

16. A method of using the chromatographic process according to claim 1, wherein the method is carried out iteratively by subjecting different target fractions of a chromatogram containing the compounds of interest to the process or by subjecting a same target fraction more than once.

17. A chromatographic process according to claim 1, wherein said process at least involves a sequence of the following steps:
(i) said cyclic accumulation phase,
wherein the at least two chromatographic columns are alternatingly operated in said first pairing of two phases of said accumulation cycle, comprising:
said interconnected phase of said cyclic accumulation phase in which an outlet of a first upstream column or group of columns is fluidly connected to an inlet of a second downstream column or group of columns such as to transfer at least a fraction of the compound of interest from the upstream column or group to the downstream column or group of columns, followed by
said disconnected phase of said cyclic accumulation phase, in which the first upstream column or group of columns and the second downstream column or group of columns are not fluidly connected, wherein at least one of the columns or group of columns is fed with said mixture via its inlet, and wherein via the outlet of at least one of said first and/or second column or group of columns the at least one further compound, which is not of interest, is discharged from the system;
wherein after said first pairing of two phases forming said accumulation cycle, the first and second column or group of columns exchange positions to undergo next interconnected and disconnected phases to form a full accumulation cycle; and
wherein via the outlet of at least one of said first and/or second column or group of columns in at least one of said phases the at least one further compound, which is not of interest, is discharged from the system;
wherein said two phases of the cyclic accumulation phase are carried out sequentially M times with M >1;
(ii) said cyclic separation phase,
wherein the at least two chromatographic columns are alternatingly operated in said first pairing of two phases of the separation cycle, comprising:

said interconnected phase of said cyclic separation phase in which an outlet of a first upstream column or group of columns is fluidly connected to an inlet of a second downstream column or group of columns such as to transfer at least a fraction of the compound of interest from the upstream column or group of columns to the downstream column or group of columns, followed by said disconnected phase of said cyclic separation phase, in which the first upstream column or group of columns and the second downstream column or group of columns are not fluidly connected, wherein none of the columns or group of columns is fed with mixture via its inlet, but wherein via the outlet of at least one of said first and/or second column or group of columns the at least one further compound, which is not of interest, is discharged from the system;

wherein after said first pairing of two phases the first column or group of columns and the second column or group of columns exchange positions to undergo a next pairing of two phases comprising said interconnected and disconnected phases to form a full separation cycle;

wherein said two phases of the cyclic separation phase are carried out sequentially N times with N ≥0; and (iii) said elution phase, in which from the column or group of columns, which at an end of phase (i) or, in case of N>0 at an end of phase (ii) contains the at least one compound of interest, said at least one compound of interest is extracted via the outlet.

18. A chromatographic process according to claim 1, wherein in the interconnected phase of the accumulation phase (i) the properties of the stream exiting the upstream column or group of columns are changed, by introducing buffer, solvent and/or modifier into the fluid path between the upstream column or group of columns and the downstream column or group of columns.

19. A chromatographic process according to claim 1,
where the compound of interest is a weakly adsorbing fraction of the chromatographic elution profile, wherein in the disconnected phase of the cyclic accumulation phase (i), and in case of N>0 also of the cyclic separation phase (ii), the column or group of columns which is not fed with mixture is operated so as to elute the at least one further compound, which is not of interest, and is also equilibrated, and/or where the compound of interest is a strongly adsorbing fraction of the chromatographic elution profile, in the disconnected phase of the cyclic accumulation phase (i), and in case of N>0 also of the cyclic separation phase (ii), the column or group of columns which is not fed with mixture is operated so as to be equilibrated, and the column or group of columns which is fed with mixture is operated such as to elute the at least one further weaker adsorbing compound, which is not of interest or to wash out at least one further weaker adsorbing compound in the subsequent interconnected phase.

20. A chromatographic process according to claim 1, where the compound of interest is an intermediately adsorbing fraction in the disconnected phase of the cyclic accumulation phase (i), and in case of N >0 also of the cyclic separation phase (ii), the column or group of columns which is not fed with mixture is operated so as to elute at least one further compound, which is not of interest, and is also equilibrated, and the column or group of columns which is fed with mixture is operated such as to elute at least one further compound, which is not of interest, or to wash out at least one further weaker adsorbing compound in the subsequent interconnected phase, wherein in any of these cases a degree, to which next to the least one further compound, which is not of interest, also a part of the compound of interest is eluted, is adapted as a function of a desired enrichment and/or absolute concentration of the compound of interest in the final eluate of the elution phase (iii).

21. A chromatographic process to according to claim 1, wherein the elution phase (iii) comprises a change of the mobile phase composition over time.

22. A chromatographic process to according to claim 1, wherein M >6.

23. A chromatographic process to according to claim 1, wherein M >10, wherein an absolute concentration of the compound of interest in a resultant eluate of the elution phase (iii) is higher than the one in the feed mixture.

24. A chromatographic process to according to claim 1, wherein N >2.

25. A chromatographic process to according to claim 1, wherein N >4.

26. A chromatographic process to according to claim 1, wherein
in the cyclic separation phase (ii) in only every second disconnected phase at least one further compound, which is not of interest, is discharged from the system, and wherein only after four phases the first and second column or group of columns exchange positions to undergo the next interconnected and disconnected phases of the cyclic accumulation phase.

27. A method of using the chromatographic process according to claim 1, to enrich, isolate, or discover compounds of interest, wherein the process is carried out systematically on target regions of an entire chromatographic profile obtained from processing the mixture containing the compounds of interest.

* * * * *